US012746179B2

(12) United States Patent
Johnson

(10) Patent No.: US 12,746,179 B2
(45) Date of Patent: Sep. 29, 2026

(54) SYSTEMS AND METHODS FOR CONTROLLING A SAUNA

(71) Applicant: High Tech Health International, Inc., Lafayette, CO (US)

(72) Inventor: Erik Johnson, Boulder, CO (US)

(73) Assignee: High Tech Health International, Inc., Lafayette, CO (US)

( * ) Notice: Subject to any disclaimer, the term of this patent is extended or adjusted under 35 U.S.C. 154(b) by 325 days.

(21) Appl. No.: 18/427,368

(22) Filed: Jan. 30, 2024

(65) Prior Publication Data

US 2025/0107964 A1 Apr. 3, 2025

Related U.S. Application Data

(60) Provisional application No. 63/586,362, filed on Sep. 28, 2023.

(51) Int. Cl.
*A61H 33/06* (2006.01)
*G16H 10/60* (2018.01)
(Continued)

(52) U.S. Cl.
CPC ........... *A61H 33/066* (2013.01); *A61H 33/06* (2013.01); *G16H 10/60* (2018.01); *G16H 40/20* (2018.01); *G16H 40/67* (2018.01); *A61H 2033/061* (2013.01); *A61H 2201/0207* (2013.01); *A61H 2201/0221* (2013.01); *A61H 2201/5007* (2013.01); *A61H 2201/5012* (2013.01); *A61H 2201/5025* (2013.01); *A61H 2201/5035* (2013.01); *A61H 2201/5038* (2013.01); *A61H 2201/5043* (2013.01);
(Continued)

(58) Field of Classification Search
CPC .................. A61H 33/066; A61H 33/06; A61H 2033/061; A61H 2201/0207; A61H 2201/0221; A61H 2201/5007; G16H 40/67; G16H 40/20; G16H 10/60
USPC .............................................................. 4/524
See application file for complete search history.

(56) References Cited

U.S. PATENT DOCUMENTS

| | | | | |
|---|---|---|---|---|
| 2011/0046702 | A1* | 2/2011 | Duncan | A61H 33/06 607/96 |
| 2020/0016029 | A1* | 1/2020 | Guilfoyle | A61H 33/0095 |

(Continued)

FOREIGN PATENT DOCUMENTS

| | | | | |
|---|---|---|---|---|
| DE | 202004009904 U1 * | 9/2004 | | A61N 5/06 |
| JP | 7436739 B1 * | 2/2024 | | E04H 1/12 |

(Continued)

*Primary Examiner* — Huyen D Le
(74) *Attorney, Agent, or Firm* — Fountainhead Law Group, PC

(57) ABSTRACT

Embodiments of the present disclosure include techniques for improving the functionality and operation of a sauna. In one embodiment, a sauna includes an automated warm up mode. Some embodiments may include lowering EMF in a sauna, configuring a sauna over a network, wirelessly controlling and configuring a sauna, as well as a Sauna Cloud system for managing and operating many saunas at potentially many different locations. Some embodiments may include some or all of a fan, heater, temperature sensor, and/or CO2 control, for example. In some embodiments, a sauna monitors a human body in the sauna and adjusts settings of the sauna to improve the health of the user.

19 Claims, 10 Drawing Sheets

(51) Int. Cl.
*G16H 40/20* (2018.01)
*G16H 40/67* (2018.01)

(52) U.S. Cl.
CPC ................ *A61H 2201/5046* (2013.01); *A61H 2201/5048* (2013.01); *A61H 2201/5082* (2013.01); *A61H 2230/50* (2013.01)

(56) References Cited

U.S. PATENT DOCUMENTS

| | | | | |
|---|---|---|---|---|
| 2025/0107963 | A1* | 4/2025 | Johnson | A61H 33/06 |
| 2025/0295556 | A1* | 9/2025 | Dragseth | A61H 33/066 |

FOREIGN PATENT DOCUMENTS

| | | | | |
|---|---|---|---|---|
| WO | WO-2021001067 | A1 * | 1/2021 | A61H 33/066 |
| WO | WO-2023224515 | A1 * | 11/2023 | H05B 3/48 |

* cited by examiner

SYSTEMS AND METHODS FOR CONTROLLING A SAUNA

CROSS REFERENCE TO RELATED APPLICATIONS

This application claims priority to U.S. Provisional Patent Application No. 63/586,362, filed on Sep. 28, 2023, the entire disclosure of which is hereby incorporated herein by reference.

BACKGROUND

The present disclosure relates generally to saunas, and in particular, to systems and methods for controlling one or more saunas.

A sauna, or sudatory, is a small room or building designed as a place to experience dry or wet heat sessions. Typically, saunas are found at an establishment with one or more of these facilities, such as a spa. Although more and more consumers are purchasing saunas for their homes for personal use. Some saunas use infrared energy to heat the occupants. The steam or infrared, and high heat make the bathers perspire. A thermometer in a sauna is typically used to measure temperature; a hygrometer can be used to measure levels of humidity or steam.

Home saunas are becoming more popular. However, managing the workings of a sauna may be time consuming and undesirable for personal use.

The present disclosure pertains to improved systems and methods of controlling a sauna for a range of applications.

DETAILED DESCRIPTION

Described herein are techniques for controlling a sauna. In the following description, for purposes of explanation, numerous examples and specific details are set forth in order to provide a thorough understanding of some embodiments. Various embodiments as defined by the claims may include some or all of the features in these examples alone or in combination with other features described below and may further include modifications and equivalents of the features and concepts described herein.

Features and advantages of the present disclosure include a number of automation and therapeutically beneficial techniques for saunas.

Figure 1:
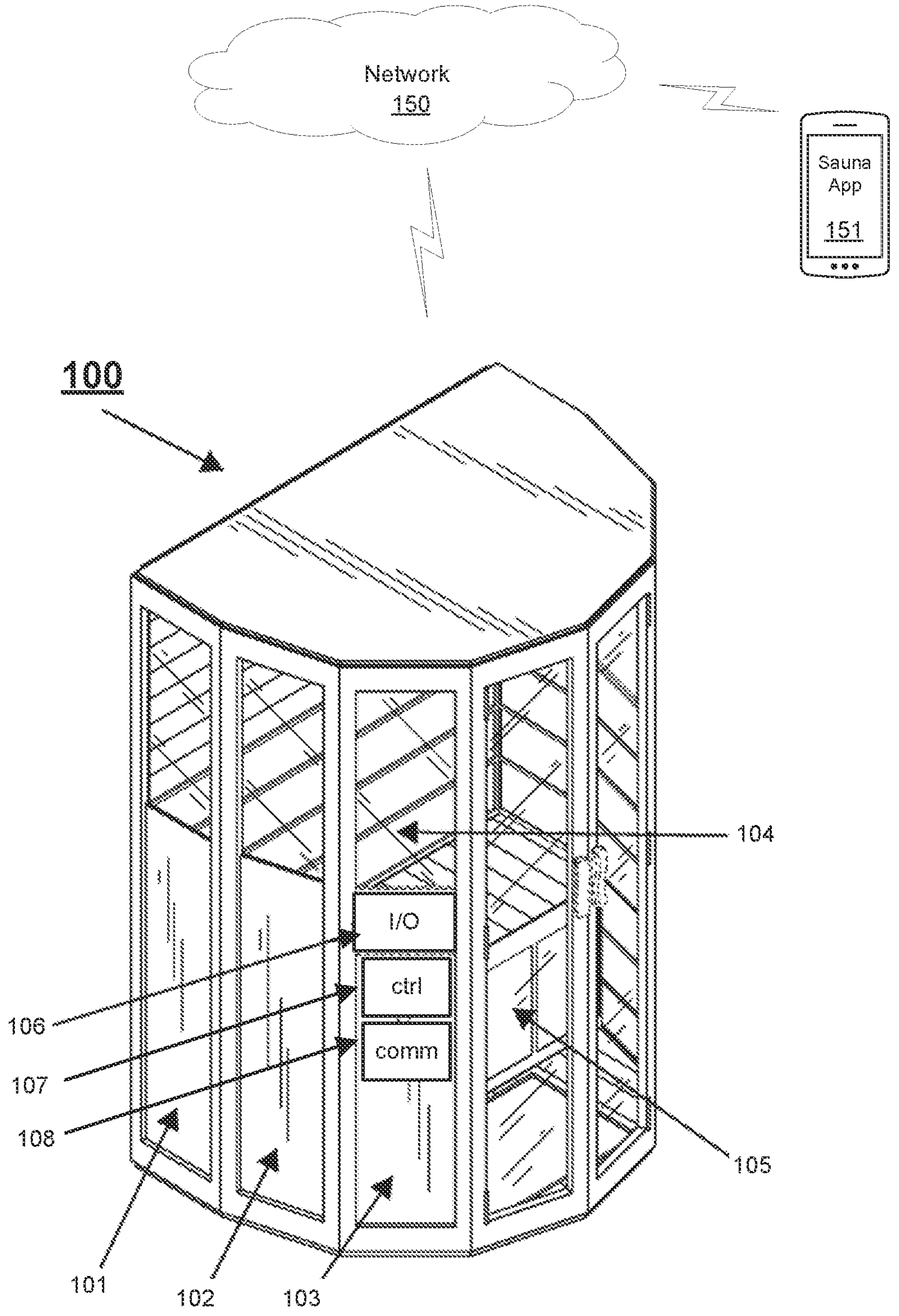
FIG. 1 illustrates a system including a sauna according to an embodiment.

FIG. 1 illustrates a system including a sauna according to an embodiment. Sauna 100 includes a room 104 and at least one heating apparatus 105 (e.g., an infrared heater). The room has a plurality of walls (e.g., 101-103). The plurality of walls form an internal space in which a human body may be heated. Heating apparatus 105 may be located on one of the walls, such as the back wall, of the sauna 100. In fact, many of the panels may be equipped with heaters to heat the body of a person. Additional heaters may be placed at the foot of the seating bench as well or in other locations, for example. Heaters 105 radiate heat toward the internal space 104 of sauna 100. Sauna 100 may include temperature sensors (not shown) placed at various locations around the sauna to measure the temperature inside the sauna.

In this example, sauna 100 includes a controller circuit ("ctrl") 107, an input and/or output device (I/O) 106, and communication circuit 108. The communication circuit may be used to couple the sauna to a network, such as the Internet, to perform some of the techniques described herein. Communication circuit 108 may be a wireless communication circuit, for example, such as a Bluetooth circuit or an IEEE 802.11 circuit (aka, "WiFi"). Using communication circuit 108, sauna 100 may be coupled to a network 150 to communicate with other electronic systems as described herein. In one embodiment, sauna 100 communicates with network 150 wirelessly, although in other embodiments sauna 100 may communicate with network 150 using a wired connections (e.g., Ethernet). In some embodiments, a mobile device 151, such as a cellular phone, tablet computer, or personal computer, may run software (e.g., an Application or "App") for configuring sauna 100 remotely as described further below. A cell phone app, for example, may be used to configure a variety of features of the sauna. I/O 106 may be used to either receive direct inputs from a user to configure the sauna, provide direct outputs to a user about the sauna's status, or both. In some example embodiments, I/O 106 is a touch screen display mounted to the sauna.

Electronic circuits in the sauna may be controlled by controller circuit 107. Controller circuit 107 may comprise one or more microcontrollers or microprocessors, for example, and may be implemented using a variety of architectures. Controller circuit 107 may include memory, such as random access memory (RAM) or persistent memory (e.g., solid state device ("SSD") memory or magnetic drive), for example. Controller circuit 107 may turn the sauna on or off, receive inputs from temperature sensors, and control the time heaters 105 are turned on commensurate with the heating and temperature requirements configured by a user. Features and advantages of the present disclosure include a sauna that includes a "warm up" mode that users can initiate (e.g., locally or remotely). During a "warm up mode," controller circuit 107 may increase the temperature of the sauna to a first predetermined temperature and then hold that temperature until a user initiates a session. During the session, controller circuit 107 may configure the heaters to perform a variety of heating algorithms, which may be predetermined and selected by a user or created by the user, for example. Warm up mode may increase the temperature of the sauna from an initial temperature to an intermediate temperature. The intermediate temperature may be warm enough to not be cold (e.g., relative to air temperature outside), for example. A minimum warm up mode temperature setting is the fastest the sauna will get to a warmer temperature (starting at a room temp) to be comfortable and effective for a user. Advantages of warm up mode include improved energy efficiency because the sauna is not being raised to an unnecessarily high temperature and going unused. This technique is also healthier for a user than entering a sauna at room temperature (which may be very cold) or waiting for the temperature to get all the way to a final session temperature, for example.

One challenge with sauna operation pertains to radiation of electric and magnetic fields (EMF). Electronic circuits in the sauna generate EMF, and it is desirable to minimize the amount of EMF a user is exposed to when using the sauna. One challenge with adding features to a sauna is the additional electronics create undesirable EMF during sauna use. In one embodiment, the present disclosure includes a technique for incorporating complex electronics while minimizing EMF. For example, initially, the sauna may be fully off and a user may desire to use the sauna in the near future. The user may send the sauna an initiation signal to start the warm up mode, for example. Controller circuit 107, which is configured to control the sauna, receives a first initiation signal. In some embodiments, the first initiation signal may be entered in an App on a mobile device and the first initiation signal is received in the controller 107 thru a wireless communication circuit. For example, the first initiation signal may be embedded in a Bluetooth or 802.11 (WiFi) signal received by the communication circuit and coupled to the controller.

In response to the first initiation signal, the sauna is configured in a warm up mode. During warm up mode, the controller circuit 107 increases the temperature inside the sauna. The controller circuit may activate one or more heaters and sense temperature through one or more temperature sensors and control the increase in temperature over time, for example. Controller circuit 107 may detect when the temperature inside the sauna meets a first predefined temperature (e.g., 100 degrees F.). In response to detecting the first predefined temperature, controller circuit 107 may maintain the first temperature (e.g., warm up mode is complete and the system enters a pre-session mode waiting for a user to enter the sauna and initiate a full session). When a user enters the sauna and initiates a session, the controller circuit may receive a second initiation signal (e.g., indicating that the user is starting a full session). The second initiation signal may be received in the controller circuit 107 from a user (e.g., start session). In some embodiments, the second initiation signal is received through an input device coupled to the controller circuit 107, and in other embodiments the second initiation signal is embedded in a wireless signal received in the wireless communication circuit (e.g., received from a user through a cell phone). In response to receiving the second initiation signal, the controller circuit 107 may advantageously disable a plurality of electronic circuits in the sauna to reduce electromagnetic radiation inside the sauna. Advantageously, the additional circuitry used to enhance the features of the sauna may be shut down in whole or substantially in part to reduce EMF inside the sauna during the period of time a user is in the sauna experiencing a session, for example. In particular, in some embodiments, wireless communications circuits for connecting the sauna to a network or a mobile device may be disabled to reduce EMF in the sauna. Wireless communication circuits use EMF to communicate information, and many users may desire that a sauna environment be free of all such wireless EMF, for example.

Further, controller circuit 107 may start increasing the temperature inside the sauna according to the session parameters specified by the user (as described in more detail below). As the temperature increases from the first predefined temperature (aka, warm up temperature), the controller circuit 107 may detect a second predefined temperature inside the sauna greater than the first predefined temperature (e.g., a session temperature). In response to detecting the second predefined temperature, controller circuit 107 may maintain the second predefined temperature during the session. For example, the controller circuit may prevent the sauna from exceeding the second predefined temperature, for example. In some embodiments, the second predefined temperature may vary over the course of the session, for example. After a predefined sauna session is complete, the controller circuit enables the plurality of electronic circuits in the sauna. Accordingly, a user may control the sauna through their mobile device again.

Figure 2:
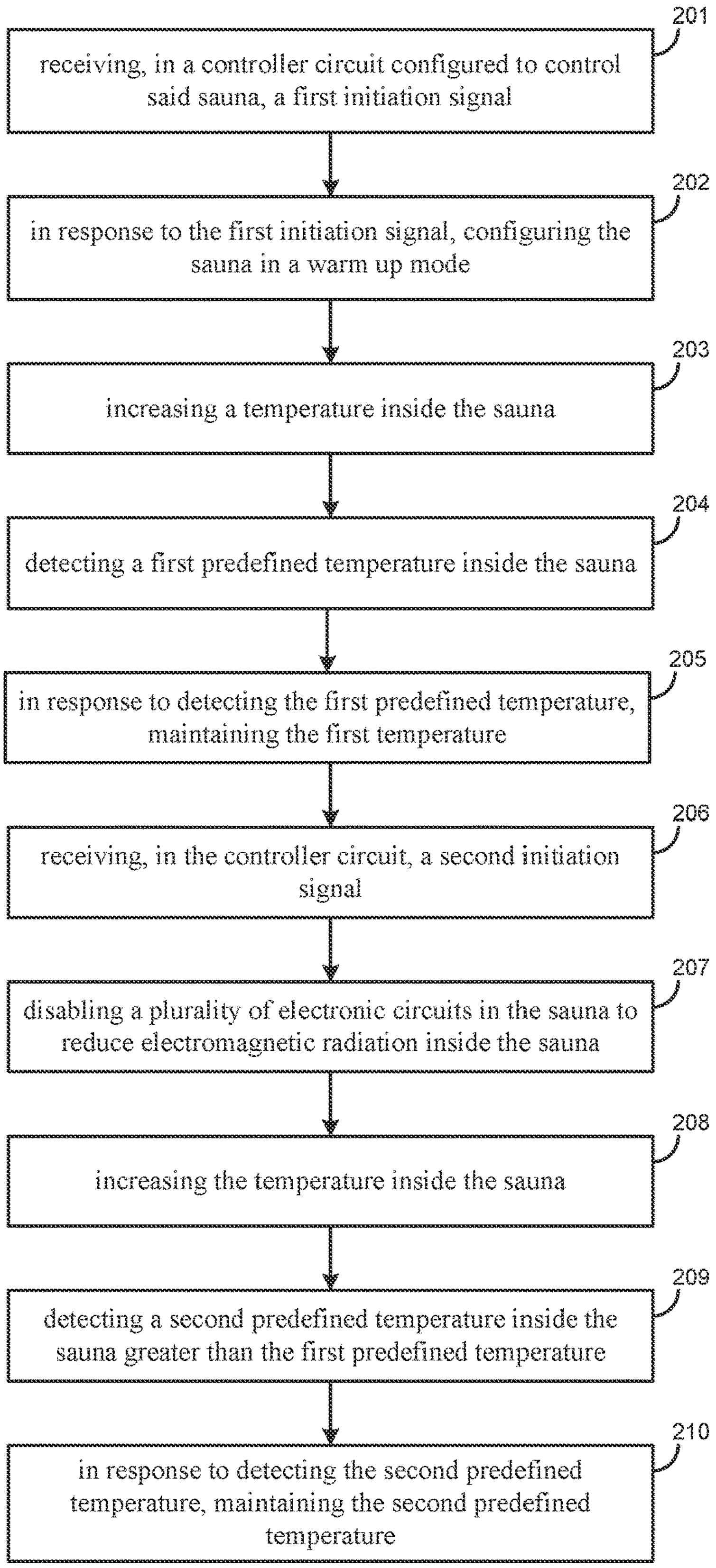
FIG. 2 illustrates method of controlling a sauna according to an embodiment.

FIG. 2 illustrates method of controlling a sauna according to an embodiment. At 201, a controller circuit configured to control the sauna receives a first initiation signal. At 202, in response to the first initiation signal, the sauna is configured in a warm up mode. At 203, a temperature inside the sauna is increased. At 204, a first predefined temperature inside the sauna is detected. At 205, in response to detecting the first predefined temperature, the first temperature is maintained. At 206, the controller circuit receives a second initiation signal. In response to receiving the second initiation signal, the controller circuit disables a plurality of electronic circuits in the sauna at 207 to reduce electromagnetic radiation inside the sauna and increases the temperature inside the sauna at 208. For example, controller circuit may shut down wireless communication circuits in the sauna to reduce EMF. Increasing the temperature may be part of transitioning from a warm up mode into one of a plurality of session modes selected by a user, for example. At 209, a second predefined temperature greater than the first predefined temperature is detected inside the sauna. The second predefined temperature may be one of multiple temperatures that are part of a session, for example. At 210, in response to detecting the second predefined temperature, the second predefined temperature is maintained. In some embodiments, the sauna may maintain different temperatures during a session.

Figure 3:
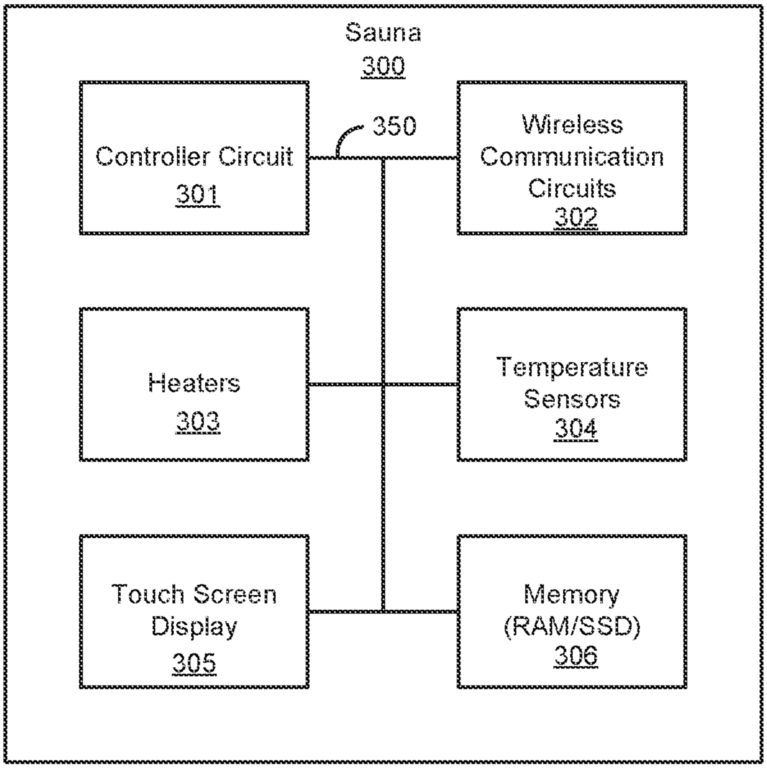
FIG. 3 illustrates components of a sauna according to an embodiment.

FIG. 3 illustrates components of an example sauna according to an embodiment. As illustrated here, a sauna 300 may include a controller circuit 301, wireless communication circuits 302, heaters 303, temperature sensors 304, a touch screen display 305, and memory 306 (e.g., RAM or SSD). Components 301-306 may be coupled together over an electrical interconnect 350. Interconnect 350 is illustrated here as connecting to all components 301-306 for illustrative purposes only. In practical embodiments, controller circuit 301 may have different dedicated sets of connections to wireless circuit 302, to heaters 303, to temperature sensors 304, to touch screen 305, and to memory 306, for example. A variety of architectures are possible. In some embodiments, predefined session parameters are stored in memory 306 and selected by users during use of the sauna. Session parameters may include temperatures, session times, etc. In some embodiments, users create profiles and store customized session parameters, which may be modifications of the predefined session parameters, for example.

In one embodiment, a particular sauna may store temperature data over a plurality of cycles of a time period occurring after the first initiation signal and before detecting the first predefined temperature inside the sauna. The controller circuit 301 may determine, based on the stored temperature data, a warm up time for a particular sauna. For example, it may be desirable to configure the sauna to be warmed up at a particular time. For instance, a person may use their phone app to remotely tell the sauna to start warming up at a particular time or they could tell the sauna to be warmed up by a particular time. When telling the sauna to be warmed up by a particular time, the sauna would have to consider the environment's starting temperature and history data for that sauna stored in memory. The history is useful because every sauna has variable thermal properties. For example, particular heaters may vary in power (e.g., each of 6 or more heaters varies in accuracy by +5/−10%, which is then further altered by AC voltage variation of 113Vac-130Vac). Additionally, the environmental conditions and location of each sauna (e.g., under an air conditioning or heater duct) might change how the sauna is able to heat up even further. Embodiments of the present disclosure store temperature data for the warm up time, the sessions, or both, and use the stored temperature data to adjust the heating controls. Accordingly, the stored temperature data may be used to control the heaters to change the temperature of the interior of the sauna such that a target warm up mode temperature is obtained by or within a certain time.

Figure 4:
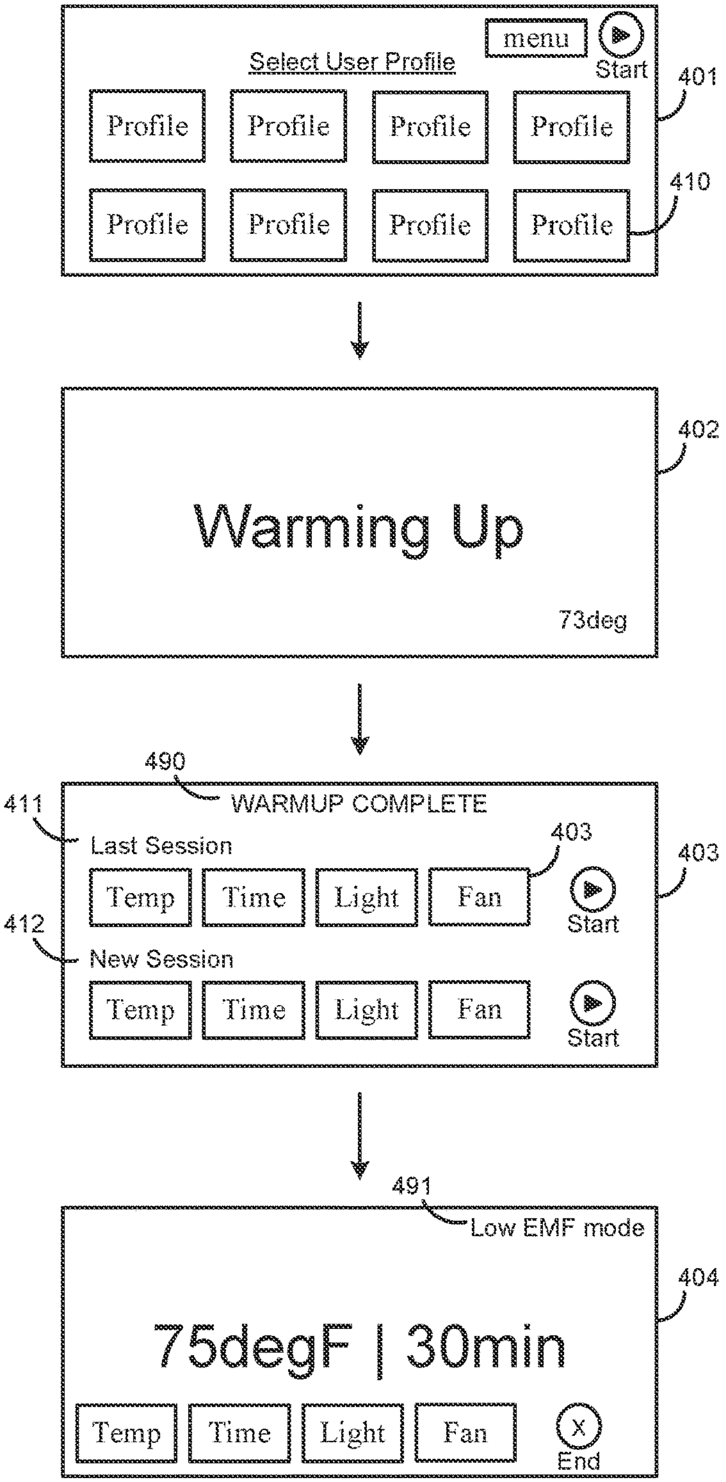
FIG. 4 illustrates a user interface for a sauna according to an embodiment.

FIG. 4 illustrates a user interface for a sauna according to an embodiment. As mentioned above, saunas take time to warm up and people like to be able to remotely control what their sauna does by an app on their phone. Sauna remote control by a phone over the Internet requires that a person's sauna be connected to Wifi, Bluetooth, or other wireless connection. When the sauna is connected to WiFi, there is a WiFi transmitter very close to the person sitting in the sauna, exposing them to that additional EMF. The present system design provides a way of having both the ability to remotely control the sauna and not exposing the user of the sauna to the additional EMF from a wireless connection, and in a way that is transparent to the user. For example, traditional saunas have a set temperature (such as 170 F) and the person gets in at that temperature and the sauna maintains that temperature. Features and advantages of the present disclosure include a "Warmup Mode" that pre-heats the sauna only to a temperature that is minimum for comfort when getting in (such as 100 F). The person uses the sauna between that temperature and a pre-set maximum temperature (or session temperature) in a way that is transparent to the user.

For example, initially a user selects a profile 410 from a plurality of profiles from Start Screen as illustrated at 401 and hits "Start" (the first initiation signal). This may be done in a mobile phone app or directly in the sauna user interface, for example. The sauna then enters Warmup Mode as illustrated at 402, where it pre-heats to a first temperature (e.g., a preset minimum comfortable temperature). When the internal temperature is at the warm up temperature, the sauna may generate a signal indicating warm up mode is done and hold the temperature at the first temperature. During a time period after the first initiation signal (e.g., start of warm up mode) and before detecting the first predefined temperature inside the sauna (e.g., end of warm up mode), the system may generate a first signal indicating a first warm up mode of operation is in progress. In some embodiments a color light might indicate warm up mode. In one embodiment, the display may change color (e.g., to green and display WARMING UP as illustrated at 402), for example. In other embodiments, a sound or song may play to indicate warm up mode to a vision impaired user.

Upon detecting the first predefined temperature inside the sauna (e.g., end of warm up mode), the system may generate a second signal (e.g., WARMUP COMPLETE as illustrated in FIG. 4 at 490) indicating completion of the warm up mode. For example, once the sauna has reached its pre-heat temperature, a song may stop, or a color light may change (e.g., back to white) to indicate to someone outside of the sauna that warm up mode has completed. The sauna maintains this temperature without increasing. Once the user is ready to enter the sauna, they may choose the settings for the sauna session they will have and hit the start button as illustrated at 403. The user can choose the same settings as the previous session at 411, choose a new session at 412 (e.g., custom or default), or be offered a suggested session as described in more detail below.

After hitting the start button from the Warmup Complete screen, the "No-EMF Mode" begins and the person uses the sauna during the session. In "No-EMF Mode", wireless circuits (e.g., WiFi and Bluetooth) are turned off until the session comes to an end. In one embodiment, after the second initiation signal (e.g., regular session start) and before disabling a plurality of electronic circuits, the controller circuit sends session information (e.g., wirelessly to a mobile device) comprising: an indication the sauna is in session, a plurality of sauna settings, and a finish time for a session. Accordingly, before the wireless circuits shuts off, the remote app may be updated to show that the sauna is in session, what its settings are, and when it will finish. This technique advantageously allows users to see the session settings after the phone app loses its ability to control the sauna during this time.

In screen 404, the controller sends session information to the display, displaying temperature and remaining time in the session, and from which they would be able to adjust settings (e.g., temperature, time, lighting, fan) during a session. Further, during the session time period (after the second initiation signal), the system may generate a third signal (e.g., Low EMF Mode 491) indicating a low-EMF mode of operation. In various embodiments, the previously mentioned first, second, and third signals are displayed on a touch screen display coupled to the sauna. In some embodiments, one or more of the first, second, and third signals are colored lights, for example, as mentioned above. After the session ends, the display generates a Session Complete screen as wifi and Bluetooth are automatically turned on again returning control of the sauna to the remote control phone app.

Figure 5:
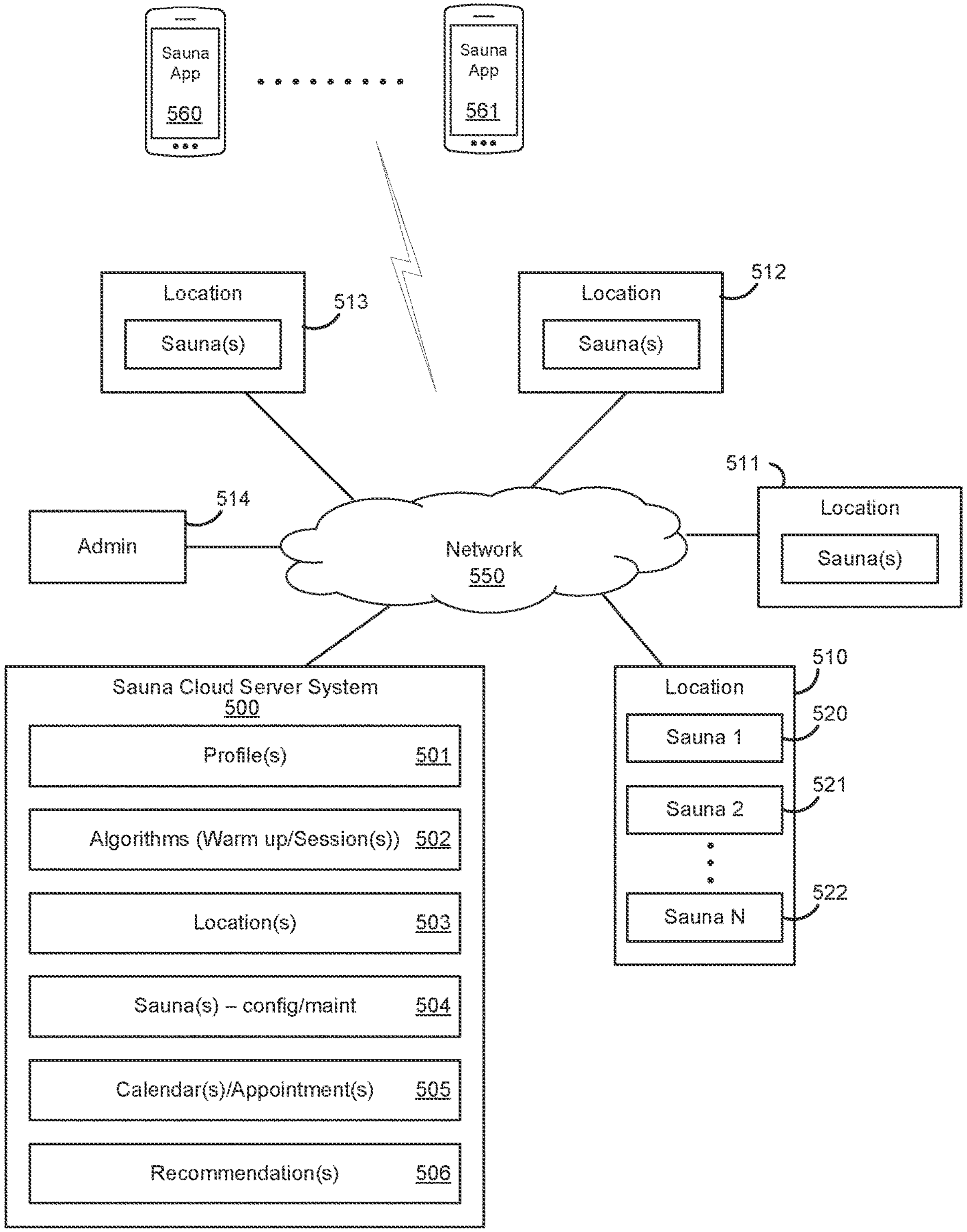
FIG. 5 illustrates a sauna cloud server system according to an embodiment.

FIG. 5 illustrates a sauna cloud server system according to an embodiment. Saunas are often placed in day-spas, medical clinics, medical spas, and homes. Organizing, maintaining, and operating many saunas can be challenging for non-experts. Features and advantages of the present disclosure include a sauna cloud server system 500 (aka, Sauna Cloud). Sauna Cloud 500 provides for central management and control of a wide variety of sauna related activities. Sauna Cloud 500 may be used to manage and control saunas at different locations 510-513, where each location may have one or multiple saunas, for example, such as saunas 520-522 at location 510. Sauna Cloud 500 may reside on one or more computer servers in a cloud computer system. In some embodiments, Sauna Cloud 500 is configured to run on a web server system, such as Amazon Web Services (AWS), Microsoft Azure, or Google Cloud, for example. Cloud computers may be configured with Sauna Cloud software for performing the techniques described herein. Sauna Cloud 500 may include profiles 501 of users of the various saunas, including preferences, sessions, usage history for each user (e.g., previous sessions selected and custom sessions), environmental data, health data, physical health goals, messaging information (email or cell phones), music selections, appointments, or the like. Sauna Cloud 500 may include various control algorithms 502 for controlling a sauna, such as algorithms for warm up mode, session algorithms, and other sauna control information. Sauna Cloud 500 may include location information 503, which may include information about a home or business where the sauna is located. Sauna Cloud 500 may include information about specific saunas 504, such as particular configuration information (e.g., components of each sauna, software versions, and hardware/software configurations), environmental information (e.g., observed temperatures or historical operating data), and maintenance data (e.g., observed errors, maintenance history, maintenance schedule, spare parts, etc.). Sauna Cloud 500 may include calendaring and/or appointment software 505 to allow businesses to schedule time in each sauna on-line and coordinate maintenance, for example. Sauna Cloud 500 may include a recommendation software module 506 to suggest sessions and operating conditions that are safe for new users, for example.

In some embodiments, a user profile, sauna, and location may be associated. For example, a user's profile may be analyzed for the particular sauna 521, and the operating conditions of the sauna optimized for the particular user. The location 510 may be used in conjunction with the calendar/appointment module to schedule time in the particular sauna, and to make sure the user's time in the sauna does not conflict with another user or maintenance. Information about the location 510 in Sauna Cloud 500 may include billing information so the user can automatically pay for the use of the sauna at the location 510, for example. Additionally, one or more algorithms 502 may be associated with particular saunas (e.g., where different algorithms are compatible with different sauna configurations) and offered to the associated user for selection or recommendation. Stored data about particular saunas may be applied to the associated algorithms and used to automatically modify the algorithms (e.g., by adjusting a warm up time based on a particular sauna's environmental conditions as mentioned above). A recommendation system, for example, may retrieve profile information, associated saunas, locations, and algorithms and adjust operating conditions of the sauna automatically. In one embodiment, an algorithm (e.g., a machine learning algorithm) may receive some or all of the above information and adjust warm up time, session time, temperature, humidity, or other parameters to optimize the users experience (e.g., health goals, minimum time spent in the sauna for maximum health results, etc.).

Instances of calendar/appointment module 505 may be associated with different entities (e.g., health clubs, spas, or even families or shared living arrangements where different users want to schedule time in the sauna). Accordingly, users may synchronize personal calendars with the calendar/appointment module for particular saunas and/or locations to streamline sauna use.

Users may access a variety of information and control setting for any sauna associated with them in Sauna Cloud 500. If calendar/appointment module 505 indicates a particular user has access to a particular sauna associated with a particular location (e.g., and the user has paid the business for the sauna's use), Sauna Cloud 500 may grant access to the user for a particular sauna and allow the user to select algorithms 502 (e.g., configure warm up times and sessions details), play music from their profile, customize lighting in the sauna, or the like). Before and after the user's appointment time period, the user may be locked out of applying custom parameters and settings to the particular sauna, for example.

In one embodiment, a profile may be an administrator profile. An administrator profile may have additional configuration and control access to particular saunas. For example, a profile with administrative rights to all saunas at location 511 and 512, which may be owned by the same business, may have access to perform built in self-test scripts, which may be stored as part of the sauna's configuration and maintenance module 504, that can be run on each sauna at each location, for example. In some embodiments, administrators may access Sauna Cloud through a administrator portal 515 running on a desktop or laptop computer or even a mobile computing device, such as a mobile phone or tablet computer, for example. Administrator portal 514 may comprise an application (app) or client side software component that interfaces with server side component to access and manipulate functionality of Sauna Cloud 500, for example.

As an example, remote control (web-based, app) for multiple saunas can be tailored to businesses to enable them to be centrally controlled, for example, using warm-up mode or predictive warm-up mode to match the business's appointment schedule. In this case, remote control may remove selected controls from the user inside the sauna so that users do not extend their sessions beyond what a recommended maximum time limit (e.g., for health or sauna operational reasons) or beyond a duration they have paid for. Suggested sessions (described further below) may enable inexperienced spa owners to ramp up use of the sauna in the safest way possible. History of use for each user may be used to make recommendations, for example. As another example, Sauna Cloud may automatically turn on a fresh-air fan included in the particular sauna config/maint module 504 (when available), for example, to rapidly cool down the saunas between sauna sessions automatically to facilitate successive appointments or alert cleaning crews (e.g., with automated messages) that a sauna needs to be cleaned between uses. This is just one example of how sauna configuration information 504 may be used to impact scheduling (e.g., saunas with fans may be scheduled for use closer together than saunas without fans). Remote control (by app, website, whatever) may further enable remote sending of messages to a particular sauna in use (e.g., reminding them of things particular to the user based on the profile information, such as suggesting they do breathing exercises, they have a phone call, advertisements for other things in the spa or clinic, their massage therapist is ready for them, etc). Different sounds/music could be sent to specific saunas per a user's request and profile or the business's choice and location information 503, for example.

As indicated above, another aspect of the present disclosure includes self-diagnosing sauna system problems and facilitating maintenance and repairs. In one embodiment, a sauna runs a self-diagnostic program using a local controller circuit to identify system failures and identified failures trigger automated repair instructions to the user, e.g., if cables become disconnected and then an algorithm walks a person through correcting them. If the person cannot solve the problem, the sauna may automatically contact customer service and open a customer service case, for example. In one embodiment, self-test may be initiated remotely (e.g., over a network and/or controlled by Sauna Cloud described above). Such a test may include running the sauna through a warmup test to determine how fast the sauna warms up. This information may be used to identify if the sauna might have a heater that has failed or is disconnected (e.g., if the sauna is heating up slowly). The sauna might also perform a test in the background during any mode of operation, and it would be part of self-identifying if a part of the sauna is not assembled correctly, for example.

It is to be understood that the cloud based system described in FIG. 5 may be used to store data, implement algorithms, and perform one or more of the various techniques disclosed herein.

Figure 6:
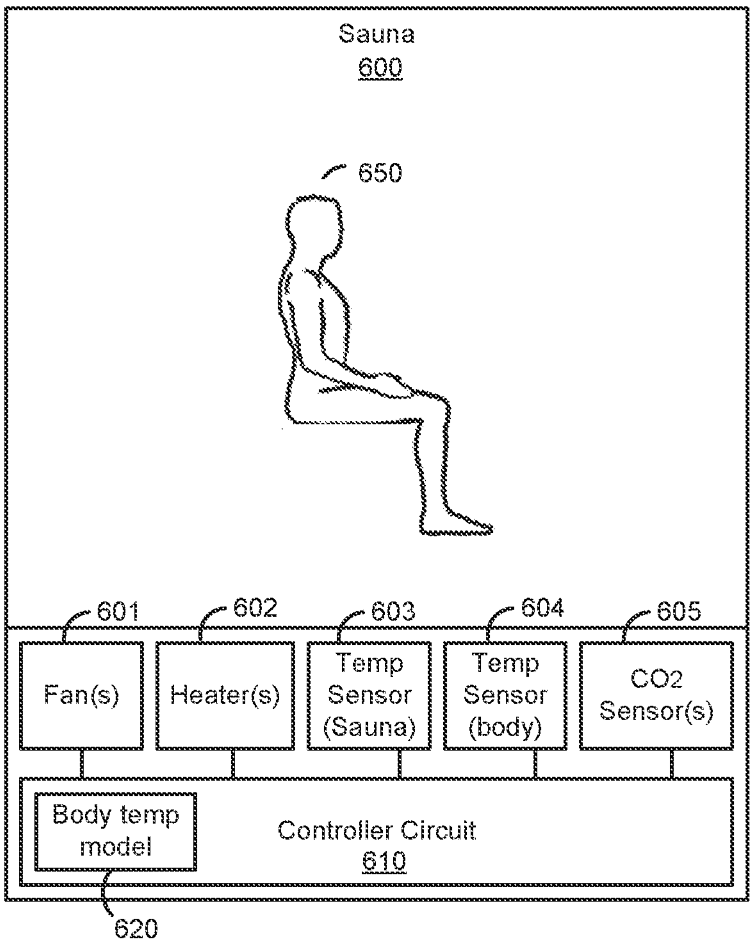
FIG. 6 illustrates controlling a sauna according to another embodiment.

FIG. 6 illustrates controlling a sauna according to another embodiment. Another aspect of the present disclosure includes controlling a sauna to obtain health benefits by adjusting sauna operating parameters based on measured inputs of a user's body. For example, a sauna may be used to change a person's body temperature. Embodiments of the present disclosure may allow users to configure the sauna to measure and control certain body parameters. For instance, sauna 600 may include a fan 601, one or more heaters 602, a sauna interior temperature sensor 603, and in some example embodiments, a body temperature sensor 604, one or more of which is controlled by controller circuit 610. In some embodiments, body temperature is determined without direct physical sensing as described in more detail below. Controller circuit 610 may receive body temperature data and use that data to determine a person's received benefits from using the sauna. For example, body temperature may be measured directly by sensor 604 or determined indirectly by sensor 603 and a model 620 that correlates the sauna temperature to a body temperature. In some embodiments, body temperature may be determined by correlating to a sauna temperature. For instance, in some embodiments, body temperature may be correlated to the sauna temperature and a session duration, for example.

Referring again to FIG. 6, another aspect of the present disclosure includes a sauna comprising one or more carbon dioxide (CO2) sensors 605, which may be used with one or more fans 601 to control CO2 levels inside sauna 600. For example, one or more in-take fans 601 are speed controlled by controller circuit 610 to control air temperature and/or CO2 levels inside the sauna. For example, fans may be configured to push in the least amount of air to maintain CO2 levels below a threshold. Fans 601 may be adjusted based on the number of people in the sauna. In one embodiment, CO2 sensor 605 senses the CO2 levels and sends the information to controller circuit 610. Controller circuit 610 may be configured with a maximum allowable CO2 level (a CO2 threshold) and may adjust the fan speed to maintain the CO2 level below the threshold value, for example. In other embodiments, which may not include a CO2 sensor, the controller circuit 610 receives a number of users and sets the threshold CO2 level based on the number of users. For example, in some embodiments, in addition to knowing the number of people in the sauna from the software, the fans may also know how long the sauna has been on and how hot it is so that it can run the fans higher toward the end of the session when the CO2 levels are higher and when the air temperature is higher and can afford to be reduced more by cooler outside air without over-cooling the sauna.

In one embodiment, the sauna session may include guided breathing exercises. In this case, the controller circuit 610 may increase the fans to maximum during such exercises, and then stop the fans for a period of time after the exercises to let the air warm up again, and then resume regular management of the air. In various embodiments, fans 601 may be configured in the ceiling and positioned to mix the air in the sauna and reduce the temperature gradient between the top of the sauna and the bottom of the sauna, for example.

Example Sauna Guide

There are tremendous possible health benefits from using a sauna. For instance, some studies have found an association between sauna use and a reduction in all-cause mortality. The benefits are related, at least in part, to a cellular adaptation to heat stress. The state of adaptation is reliant upon sufficient heat shock protein (HSP) gene transcription and the resulting proteins being produced. There are different heat shock proteins, but in general, HSPs are understood to help cells and proteins maintain homeostasis and facilitate recovery from and adaptation to stress at the cellular, organ, and whole-body level, for example. The sauna increases your body temperature and can trigger this process. Features and advantages of the techniques described herein may be used to improve such processes.

New sauna users often find that the sauna experience isn't all that good, or worse, using the sauna makes them feel sick. Poor experience demotivates people using the sauna and prevents them from achieving positive outcomes. Features and advantages of the present disclosure include software for operating a sauna designed to slowly acclimate users to longer and hotter sessions. Embodiments of the disclosure include software for operating a sauna to optimize how and/or when users use the sauna to get the health benefits they want and provide information to the users that allows them to understand how the sauna is improving their health.

Embodiments of the present disclosure may include automated acclimation and regular use of a sauna to promote use and maximize health benefits. In some embodiments, knowing the received benefits of using the sauna, an algorithm may attribute "points" to a person's history of sauna use. In some embodiments, the algorithm may subtract points based on declining benefit with time away from the sauna. The algorithm may produce a score (or "sauna score" or Sauna Fitness™), which may be used to suggest to the user the sauna settings for their next session, for example. For example, if a person starts a session for 30 minutes, then at the end of the session the user may receive (via a display or App) a message indicating how that session affected their "Sauna Score". If the person were to cancel their session at 15 minutes, then a message may indicate how their score will be affected if they finish the originally intended session versus stopping early, for example.

Using this "sauna score", we might prompt the user to use the sauna with text messages (emails, app notifications, etc) with information telling them they will lose X points if they don't use the sauna, or can gain points or maintain their score if they do use the sauna in a certain way by a certain time/date. This "sauna score" can be used to give a person virtual "awards" for achievement and to be able to compare their achievement with others.

Embodiments of the present disclosure may generate recommendations to the user for sauna system settings. For example, the system may recommend how long and what the maximum air temperature should be. The system may recommend settings according to an acclimation algorithm each time a user uses the sauna across a series of sessions until the user has become acclimated to use. In some embodiments, the user may provide feedback to the system the end of one or more sessions and the feedback may be incorporated into subsequent recommendations. For example, a user may be asked how the session felt and an adjustment is made to the recommendation on subsequent uses of the sauna. A rate of acclimation may be customized to the user, for example, by asking the user (e.g., initially on setup): how regularly do you sweat, how regularly do you do cardio exercise, and other user data. The system may output a recommendation of when to use the sauna next and may adjust the user's progress based on how and when they actually use the sauna (e.g., moving them backwards with knowledge of days of non-use).

In some embodiments, a sauna may include software comprising a startup (e.g., "Getting Started") mode that tracks completed sessions. Startup mode may take a user through a predetermined number (e.g., 20) of increasingly longer sauna sessions. The software may gradually increase the session time up to some predetermined number (e.g., 30 minutes) to gently acclimate a user. After the startup mode is completed by the user (e.g., when the predetermined number of sessions are completed), the system software may transition into guided mode (e.g., "Sauna Guide™").

Features and advantages of the present disclosure include a "guided" sauna mode software system. In guided mode, the sauna software automatically determines sauna session operating conditions as set forth according to various examples herein. For example, the system may be configured for a particular session time in the sauna to maximize health benefits (e.g., prompt the user to stay in longer if user tries to end their session too soon). The system software may include a calendar system for the user to indicate how their "health" (aka, "Fitness) may change depending on when they choose to use the sauna next: on which days they will gain "Fitness", maintain "Fitness", lose "Fitness", or have totally lost "Fitness". The calendar indicates to the user the minimum session length they can expect for a particular date or session, for example.

Figure 7A:
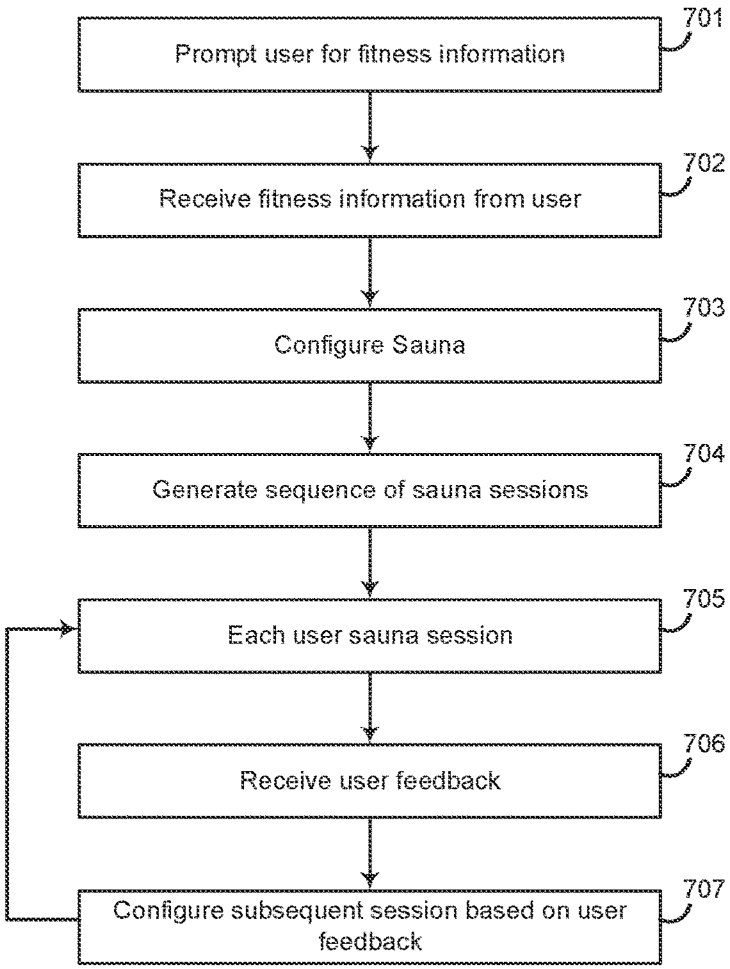
FIG. 7A illustrates a method for use in a sauna according to an embodiment.

FIG. 7A illustrates a method for use in a sauna according to an embodiment. In one embodiment, sauna settings may be generated automatically for a user when they go to use the sauna (e.g., a duration for a session and a maximum air temperature). As mentioned above, in various embodiments, software for controlling a sauna may be implemented in an application running on a mobile device, tablet, cloud computer system, or in a local sauna controller, for example. At 701, the software may prompt a user for a fitness information. In some embodiments, the system may prompt the user for a fitness level and/or a sweat frequency. For example, the software may customize a rate of acclimation for each user by asking them initially: "How regularly do you sweat?" (aka, sweat frequency) and/or "How regularly do you do cardio exercise?" (aka, fitness level), or equivalent information about the user's fitness and health to customize sauna sessions for the user. At 702, the user's fitness information is received. For example, the user may enter an indication of the fitness level and an indication of the sweat frequency. The indication may be a selection of one of a plurality of categories, numbers, or a variety of other techniques (e.g., fitness level/exercise frequency may be: none, rarely, a few times a month, a few times a week, or daily; swear frequency may be: no tolerance, never, occasionally, often). At 703, the sauna is configured with customized settings for the user. In some embodiments, the software may determine a time and a maximum temperature based, at least in part, on the response to the prompt (e.g., the fitness level and sweat frequency). The software may then configure the sauna automatically to operate at or below the determined maximum temperature for the determined time for the sauna session. The following is an example table for determining time and temperature from fitness level and sweat frequency:

TABLE 1

| | Exercise: None | Rarely | Few/month | Few/week | Daily |
|---|---|---|---|---|---|
| Sweat | A | A | A | A | A |
| No tolerance | | | | | |
| Never | A | B | B | B | B |
| Occasionally | B | B | B | C | C |
| Often | B | B | B | C | D |

In the above table, users are associated with classifications based on fitness level and sweat frequency. The classifications are A, B, C, D. The following Table 2 illustrates example time and temperatures for the classifications of Table 1.

TABLE 2

| | Duration (minutes) | Max Air Temperature |
|---|---|---|
| A | 5 | 105° F. |
| B | 10 | 110° F. |
| C | 20 | 120° F. |
| D | 30 | 130 °F. |

In the above Table 2, classifications associated with users based on the user's fitness information is, in turn, associated with session times (aka durations) and temperatures. Accordingly, the sauna session may be customized for a user based on information from the user regarding their fitness, for example, so that the operation of the sauna is customized to a user's health. In some embodiments, prompting the user further includes prompting the user to enter an age. When the system receives an age of the user, the system may further determine the duration and the temperature based on the age. For example, when the age is greater than a threshold (e.g., 50), the determined duration is a particular duration that is less than a determined duration for an age below the threshold and the determined temperature is a particular temperature that is less than a determined temperature for an age below the threshold. For example, a user above a certain age may be reclassified to a lower duration and temperature in table 2. For example, users over 50 who would otherwise be classified as C or D may be reclassified to B.

Figure 7B:
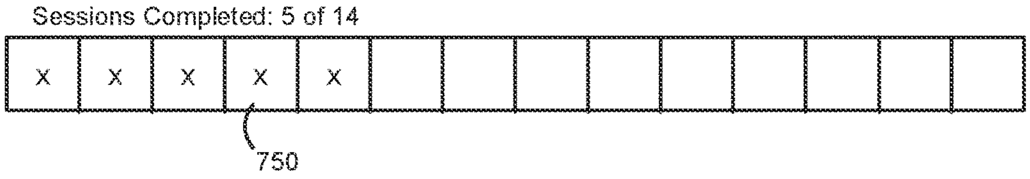
FIG. 7B illustrates a sauna display showing acclimation sessions according to an embodiment.

In certain embodiments, the software may further determine that the user is a new user of the sauna. In this case, the system may enter an acclimation mode. Additionally, at 704, the system may generate a sequence of sauna sessions over a plurality of days (e.g., in acclimation mode to acclimate a user). The sequence of sauna sessions each may have an associated duration and an associated maximum temperature. As a new user progresses from session to session, the duration and maximum temperature may be increased, for example. An initial session may have a duration and temperature generate according to the technique described above (e.g., Tables 1 and 2). Additional sessions in the acclimation sequence may increase duration and temperature over a number of days until a target sauna session duration and target sauna session temperature are achieved. In various embodiments, sauna sessions after the first sauna session may successively increase one or more of: a duration associated with the session and the temperature associated with the session. For example, in one embodiment, sauna sessions after the first session alternate increasing temperature (e.g., +2° F.) and duration (e.g., +2 minutes) until the final session is 30 minutes and 130° F. Accordingly, the number of sessions and the settings for acclimation are customized for the user. As the user moves from session to session, the software may show completed sessions 750 of the acclimation sessions in a display as illustrated in FIG. 7B, where the number of sessions for acclimation displayed to each user is customized based on the user's fitness information.

As illustrated above, sauna software may suggest new settings each time a new user uses the sauna for a series of sessions until they have become acclimated to use. In some embodiments, at the beginning of each session the user maybe be asked how they have felt since their previous session. In some embodiments, at the end of each session the user may be asked how the session felt and an adjustment is made to when they are recommended to use the sauna again. The system may give the user a suggestion of when to use the sauna next and adjusts their progress based on how and when they actually do use the sauna (moving them backwards with knowledge of days of non-use). Referring again to FIG. 7A, at 705, sauna sessions are completed by the user. At 706, user feedback is received. At 707 subsequent sessions are configured based on the user feedback.

For example, at an end of a completed sauna session, the system may prompt the user to input feedback regarding the duration associated with the completed sauna session and/or the maximum temperature associated with the completed sauna session. In response, the system receives the input from the user corresponding to the duration and/or maximum temperature. The system may configure a subsequent session duration and subsequent session maximum temperature based on the input. The input may correspond to an indication (e.g., as felt by a user) the completed sauna session was too hot, an indication the completed sauna session was too long, and one or more indications the completed sauna session was neither too hot nor too long. For example, at the end of every sauna session, the user may be asked: "How comfortable was the session?" The provided response categories may be: (a) very uncomfortable (too hot), (b) slightly uncomfortable (too long or a little too hot), (c) fine, (d) good, (c) great, for example.

Setting sauna operating parameters for subsequent sessions may be used in acclimation mode or normal (non-acclimation mode), for example. The recommended duration and maximum air temperature for a user's sauna session may depend on if the user is in an "acclimation" mode. "Acclimation" is intended for users that are first starting to use the sauna or when they have taken a long hiatus from using the sauna. As mentioned above, "Acclimation" may comprise a series of sauna sessions, each with a predetermined duration and maximum allowed air temperature. The sequence is designed to gradually acclimate the user to progressively longer and hotter sessions until they are comfortable using the sauna for at least a target duration (e.g., 30-minute sessions) and at a sufficiently high temperature. If the user reviewed the previously completed session and input category "a" (too hot), then the next session will be the session before the previously completed session in the sequence (the user will be moved back in the sequence). If the user reviewed the previous session and input category "b" (too long or a little too hot), then the recommended session repeats the previous one in the sequence.

In some cases, during acclimation mode, a user may exit the sauna before the current session is completed. In this case, the sauna software may detect the early exit and generate a message to the user indicating remaining minutes. If a user exits the sauna prior to completing a session, the system may automatically repeat the session on the next use and not progress the user toward completing the acclimation process, for example.

Sauna Guide with Sauna Score

Features and advantages of the present disclosure further include generating a score (aka, a "sauna score" or "sauna fitness score"). While the following features using sauna score are described in the context of non-acclimation mode, it is to be understood that the various features described for a sauna score could be used in acclimation mode as well. In some embodiments, sauna software may generate a score based on usage of a sauna over a time period (e.g., a number of days). The score is configured to increase based, at least in part, on use of the sauna (e.g., each session/day) and the score decreases based, at least in part, on non-use of the sauna (e.g., missed sessions/days). The score may be based, at least in part, on a change in a body temperature (e.g., core body temperature) of the user during a use of the sauna, and the changes in body temperature may be used to estimate an increase in heat shock protein production in the user, for example, or for progress toward heat acclimation of the user of the sauna, for example. For instance, body temperature may be an input to a software component that estimates when in a session the user starts producing above-normal heat shock proteins (HSP) and how much HSPs they produce over time. The software then uses the HSP estimation to determine the user's progress toward adaptation (e.g., to produce the "Sauna Fitness" score). In some example embodiments, the score may be expressed as a percentage, with 100% being the maximum score, for example. Further, the software may reduce a user's score based on non-use. Some embodiments may monitor a user's prior history of adaptation to adjust the score differently before and after 100% "fitness", for example.

Figure 7C:
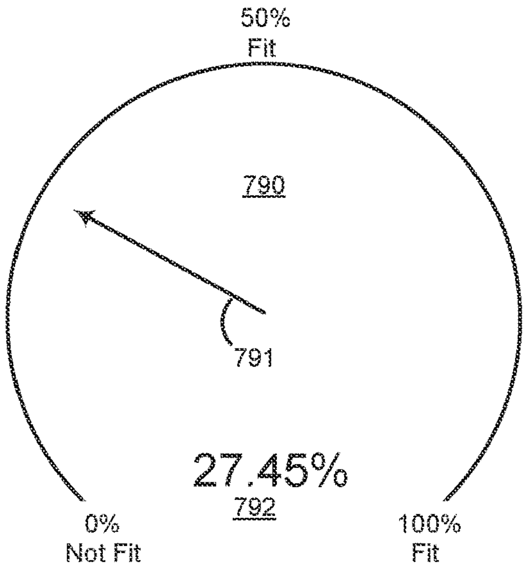
FIG. 7C illustrates a display showing a sauna score according to an embodiment.

FIG. 7C illustrates an example display showing a sauna score according to an embodiment. In this example, sauna software generates a speedometer 790 illustrating a user's current score between 0% and 100% as a radial dial 791 pointing radially outward to a partial circle. The value of the score may be presented below the radial center at 792, for example. Accordingly, sauna software may show a user their running state of cellular adaptation between 0% and 100% as a sauna fitness score. This "biofeedback" may increase or decrease based on amount of use or non-use of the sauna, for example.

Figure 7D:
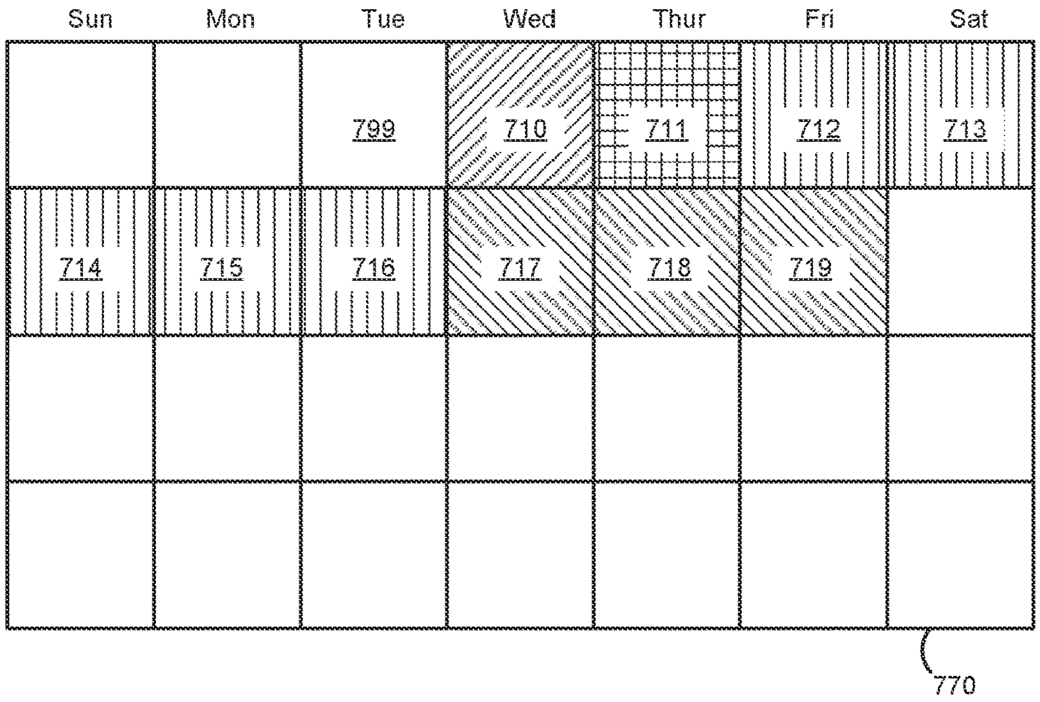
FIG. 7D illustrates a display showing the reduction in sauna score on a calendar according to an embodiment.

FIG. 7D illustrates a display showing the reduction in sauna acclimation on a calendar according to an embodiment. In some embodiments, sauna software may generate a plurality of fitness predictions over a plurality of days. The fitness predictions may indicate one or more gains in fitness, one or more constant fitness, and one or more losses in fitness over the plurality of days. The predictions may be based on the user's most recent session 799 and what the user's fitness would be if the user conducts a sauna session on one of the subsequent days, for example. Accordingly, the fitness predictions may be associated with a minimum sauna duration (e.g., the next session should be at least 14 minutes long). The plurality of fitness predictions may be displayed in sequence from highest gain in fitness to highest loss in fitness. In this example, a plurality of fitness predictions 710-719 are displayed in a calendar 770. The fitness predictions may be generated based on a most recent use of the sauna. Accordingly, when display in a calendar, the fitness predictions may span a number of days over any particular days of the year. Hence, days and months are omitted in FIG. 7D for illustrative purposes. Sauna software may determine a gradual loss in sauna acclimation after each sauna session and display the gradual loss to the user in the calendar. For example, at 710, the next day, the user may experience a gain by using the sauna the next day. At 711, the user may also experience a gain, but lower than the gain from using the sauna at 710. At 712-716, the user may achieve no gain, but may maintain a current level of sauna fitness. At 717-719, the user may begin to lose their current sauna fitness. In some embodiments, a sauna score may be calculated for a user at the end of a current session, and predictions of the score's value are displayed to a user based on subsequent sauna usage. In some embodiments, the user's sauna score is calculated based on next subsequent usage on days 710-719 to show the user what happens to their score based on one or more days of non-use. In this example, maximum gain 710, gain 711, no gain or loss 712-716, and losses 717-719 are shown using lines and hashes. However, in other embodiments different fitness predications of the plurality of fitness predictions may be displayed to a user using different colors, for example.

Example categories of fitness predictions are as follows. When the system is in acclimation mode, maximum gain may correspond to no skipped days since previous session, a gain may correspond to one skipped day since previous session, maintaining current level may correspond to when the number of completed sessions (of the initial sessions) minus half the skipped days is greater than 3, a risk of loss is when the number of completed sessions minus half the skipped days is less than 3 and greater than 0, and fitness loss occurs when the number of completed sessions minus half the skipped days is less than or equal to 0.

Next, in an example non-acclimation mode, categories of fitness predictions are as follows. Maximum gain category is associated with no skipped days from previous session. A gain category may correspond to 1 skipped day since previous session. As illustrated in further examples below, embodiments of sauna software may determine a fitness score differently after a user has achieved 100% fitness. For example, a user's score may increase faster if the user has previously achieved 100% fitness score and the user's score may decrease more slowly if the user has previously achieved 100% fitness score. For instance, in some embodiments a user may receive a maximum gain category if the user has previously achieved 100% fitness and has not fully lost it since then, and less than 2 skipped days from previous session to the next session. Similarly, if the user has previously achieved 100% fitness and has not fully lost it since, the user may receive a gain category when the fitness score is still greater than or equal to 60% after the score has been reduced for any missed days up to the next session, for example.

When more days are missed between sessions, users may maintain their fitness score, risk reducing their fitness score, and lose fitness. For example, the score may be maintained in some embodiments, when the score after missing days is determined to be less than 60% and greater than or equal to 30%. The risk of losing fitness category may correspond to the score dropping below 30% but still being greater than or equal to 2.6%. Finally, the calendar may show lost fitness when the score falls below 2.6%. It is to be understood that more or fewer categories may be associated with different numbers of missed days or different percentages or other values for fitness scores, and the above numbers are merely examples.

As mentioned above, in some embodiments, sauna session settings for subsequent sessions may be adjusted based on feedback from the user of a previous session. For instance, in some embodiments, the sauna software system may prompt a user to input feedback about how the user has felt since the previous session. In some embodiments, at an end of a completed sauna session, the sauna software system may prompt a user to input feedback about the session that the sauna software uses to adjust parameters of a subsequent sessions to that the session are customized for the user. In one embodiment, the feedback may include information regarding one or more of: how the user felt, the duration associated with the completed sauna session and the maximum temperature associated with the completed sauna session. The sauna software may receive an input from the user corresponding to one or more of: the duration associated with the completed sauna session and the maximum temperature associated with the completed sauna session. The sauna software may then configure a subsequent session duration and subsequent session maximum temperature based on the input, for example. In some example embodiments, the input corresponds to one of: an indication the completed sauna session was too hot, an indication the completed sauna session was too long, and one or more indications the completed sauna session was neither too hot nor too long.

For example, at the end of every sauna session, sauna software user interface may prompt the user with, "How comfortable was the session?" Sauna software user interface may display a number of option such as: "a) Too Hot or uncomfortable, b) Too Long (A little uncomfortable); A little too long or a little too hot, c) Fine, d) Good, or e) Great!" The displayed options may correspond to categories resulting in different subsequent session parameters. An example of acclimation mode feedback was provided above. In non-acclimation mode, a recommended minimum duration for a sauna session may be determined to be the length of a sauna session where the user's score remains the same after their sauna session. Initially, the recommended maximum air temperature may be 130° F., but that is modified depending upon how they reviewed their previous session: "a"=Previous session's temperature−5° F. (going no lower than 100° F.), "b"=Same temperature as previous session, "c" or "d"=Previous session's temperature+5° F. (not to exceed 130° F.), and "e"=Previous session's temperature+5° F. (not to exceed 140° F.).

In some embodiments, the feedback from the user may be used to recommend a next session. In the above example, if "a" is selected by a user and they just used the sauna yesterday, they will be recommended not to use the sauna today. If "a" is selected and they previously used the sauna day-before-yesterday, or "b" is selected and they just used the sauna yesterday, they will be recommended only to use the sauna if they have been feeling well, for example. If they answer "c", "d", or "e", they are recommended to use the sauna every day, for example.

As mentioned above, the sauna software may generate recommendations to not exit early and/or not stay in the sauna too long. As mentioned above, in "acclimation" mode, the system may display to the user how many minutes remain (if any) to complete this session in the sequence. If they do not complete it, they will repeat it next time. In non-acclimation mode, during a current sauna session, the system may determine an increase in the score from the current sauna session and a decrease in the score from one or more previous days of non-use of the sauna, wherein, when the increase is less than the decrease during a current sauna session: determining a remaining time so that the increase equals the decrease; and generating a message to the user indicating the remaining time. For example, if at the time a user desires to exit, the score increase from the current use is less than the score decrease from previous non-use, the system recommends they stay in the sauna the number of minutes necessary for the score increase to equal the score decrease (e.g., their fitness remains the same). If there is no duration that can achieve that, the system may determine and send a message of the amount of fitness they can recover if they stay in a number of additional minutes. However, if, at the time a user desires to exit, the score increase is greater than the score decrease from previous use, the system may generate a message to indicate how much more fitness they can gain if they stay in an additional number minutes, or a number of additional minutes it is possible for them to continue gaining "fitness". In some embodiments, if they are already at their maximum gain of fitness for the day, there is no recommendation.

In some embodiments, the sauna software may recommend against too long of a session. For example, for safety and to try to prevent heat stroke, the sauna software may generate a message to warn the user if they try to set a session duration or extend a session such that we predict their core body temperature will reach 103° F. (or if the user tries to set a duration of 90 minutes or longer).

Determining a Sauna Score

The following is one example of determining a sauna score. In some embodiments, sauna software may store profile information about one or more users. The software may monitor use of the sauna by the user associated with the profile over a plurality of days. The software may generate a score based on usage of the sauna over the plurality of days. The score increases for each use (e.g., each day of use) of the sauna and the score decreases for non-use (e.g., each day of non-use) of the sauna. Features and advantages of the present disclosure include increasing the score based on body temperature of the user during a particular use of the sauna. In some embodiments, increases in body temperature of the users during use of the sauna are used to increase the sauna score. Such increases may be based on core body temperature, for example. Increases in body temperature of the user during a particular use of the sauna may be used to estimate an increase in heat shock protein production in the user, for example. In some embodiments, increases in humidity compared to the ambient humidity, as measured by a humidity sensor, are used to increase the sauna score. Increases in humidity compared to previous sessions are used to estimate increased sweating by the user, which can be used to further estimate the user's state of heat acclimation.

As mentioned above, sauna software according to various embodiments may generate a score for each user based on sauna use. As the user spends more time in the sauna, the score increases, and non-use results in the score decreasing. In one example embodiment, the fitness score comprises a ratio of accumulated values associated with a user over the plurality of days and a maximum accumulated value. For example, the following example illustrates on technique for determining a sauna fitness score:

Fitness Score=(user's total accumulated points/total possible points over time period)×100.

In the above method, after each sauna session, points (or values) are gained for each sauna session. The sauna software accumulates and stores total points for the user. When the user completes another sauna session, the values for that session are added to the stored total. Points may be deducted (lost) for non-use, for example. The user's total accumulated points are then determined and stored. The user's total accumulated points are divided by total possible points over a time period. The total possible points may be based on a maximum amount of points possible for a session. In one embodiment, the total possible points is based on an average maximum amount of points gained for a single sauna session across a corpus of users for a particular time period (e.g., 30 minutes). The total possible points may be based on consistent sauna use without non-use for one or more days, for example. Accordingly, the fitness score calculation above is one example estimate of a user's state of heat acclimation. In one embodiment, the total possible points is one of a plurality of multiples (e.g., ×6, ××10, ×14) of the maximum points for a single use of the sauna, for example. In one embodiment, the multiples are user selectable (e.g., levels corresponding to "easy," "moderate," or "hard").

One technique for increasing the score relates to increasing points based on the user's body temperature (e.g., points gain=f (Tb) where "f" is the known functional notation and Tb is body temperature). For example, in some cases increases in body temperature may be used, and the sauna software may increase points as f (ΔTb), where ΔTb is an increasing change in body temperature. In one embodiment, an amount the score increases during the particular use of the sauna comprises a sum comprising a plurality of body temperature values corresponding to increases in body temperature at a plurality of time intervals. For example, the increase in score may be of the form Σ f (ΔTb). Accordingly, increases in score may be generated from increases in body temperature after entering the sauna, for example. In one embodiment, the time intervals are minutes and the sauna software generates a score based on changes in body temperature about every minute after entering the sauna, for example. In some example embodiments, gains in the score may be of the form:

$$\text{Points gained} = \sum [C2 * xi - C1].$$

In this example, an amount the score increases during the particular use of the sauna is based in part on a sum, over a plurality of time intervals, i, of a product subtracted from a first constant, C1. The product, C2*xi, is a plurality of body temperature values, xi, corresponding to increases in body temperature at each of the plurality of time intervals, i, multiplied by a second constant, C2. In one example embodiment, C1 is 0.754, C2 is 1.157, and the sum is from "i" (in minutes), xi is the change in the user's core body temperature at time "i" relative to the user's core body temperature just before entering the sauna (in ° C.). A minimum increase in body temperature, xi, may be set such that the product, C2*xi, is greater than or equal to the second constant, C2. For example, the above points gained formula may be invoked after an increase in core body temperature is greater than 0.652418 so that only positive values of the above formula are summed. In some embodiments, an amount of points gained (and score increase) during the particular use of the sauna may be set to a maximum value similar to as mentioned above. The points gained corresponds to an estimate of heat shock protein production above a user's baseline (or normal) heat shock protein production.

The following is an example of how decreases in scores are determined. In some embodiments, the score for a particular use of the sauna comprises a previous score minus a loss value corresponding to a time between sauna sessions plus a gained value from the particular use of the sauna. One example technique for determining losses is as follows:

$$\text{Points\_lost} = \frac{1}{2}[\text{Maximum\_points\_for\_a\_session} *$$

-continued

Number_of_days_between_sauna_sessions].

Accordingly, points gained and points lost may be combined with previously accumulated points from prior sauna sessions to produce a total points accumulated for the user as follows:

User's_total_accumulated_points = Previous_total − Points_lost + Points_gained.

The total may be set to a maximum or minimum value so the total points possible for a time period (e.g., a level) does not exceed a maximum (i.e., 100% Fitness) or fall below zero (i.e., 0% Fitness), for example.

In some embodiments, when a preexisting score is a maximum score (e.g., 100%) and a current score is less than the maximum, the system may increase an amount the score increases based on the increase in the body temperature of the user during the particular use of the sauna. The system may also decrease an amount the score decreases based on a time period of non-use. This allows the sauna software to model improved capacity of users who have obtained at or near 100% fitness to recover back from days of non-use faster as well as reduce the impact on such users to days of non-use. For example, when a user has previously achieved at or near a maximum score, gained points may be amplified. For example, if the user has previously achieved 100% Fitness and has not fully lost it since then, points gained for a session may be determine according to the following alternative formula:

Points_gained = (Points_gained_normal)/Maximum_points_for_a_session) $*F1$.

F1 is a constant (e.g., between 7 and 12 times [0.026*Total points possible for level]).

Additionally, if the user has previously achieved at or near 100% Fitness and not fully lost it since then points lost may be as follows:

Points_lost = 0.026 * Total_points_possible_for_level * days_between_sauna_sessions.

Estimating Body Temperature

In various embodiments, body temperature, such as core body temperature, may be measured using a number of known techniques (e.g., a smart watch, a body temp sensor, or the like) and used in the above formulas to adjust a sauna fitness score. Body temperature sensors may be coupled to a sauna wirelessly, for example, to provide body temperature measurements as inputs to the above algorithms, for example.

However, in other embodiments, features and advantages of the present disclose include estimating increases in core body temperature. In particular, sauna software according to various embodiments advantageously determines body temperature based on one or more of the following criteria: (i) a time difference between when the user woke up on a particular day and a start time of the particular use of the sauna on the particular day, (ii) a prior sauna use history for the user over a predetermined time period, (iii) a height of the user, (iv) a gender of the user, (v) age of the user, and/or (vi) whether or not the user used the sauna on a previous day.

Embodiments of the disclosure may train a predictive engine using a corpus of data for a plurality of users. The data may include one or more of the above criteria (i)-(vi) for each user as well as a measured body temperature at various time points during a sauna session (e.g., t0=body temp upon entering the sauna and additional body temperature measurements at regular intervals during the sauna session, such as every minute). Example predictive engines may comprise a machine learning model (e.g., a neural network), linear regression, or other suitable trainable predictive models.

For example, linear regression may be used to predict core body temperature in some embodiments. An example multiple linear regression model may be of the form:

$$y = B0 + B1 * x1 + \ldots \; Bn * xn + e,$$

where y is the predicted value (e.g., core body temperature), B0 is the y-intercept (the value of y when all other parameters are set to 0), Bi are the regression coefficients of the independent variables xi, and e is the model error. The training data is used to generate a plurality of lines for a plurality of body temperatures and produce regression coefficients for the criteria (i)-(vi) above producing a minimum error for the model. Accordingly, each coefficient Bi corresponds to one of the criteria (i)-(vi). Thus, criteria (i)-(vi) are converted to numeric values.

For example, a time difference between when the user woke up on a particular day and a start time of the particular use of the sauna on the particular day may be converted to a numeric value (e.g., a number of hours, minutes or seconds). The numeric value may then be normalized to a value between 0 and 1. Similarly, a prior sauna use history for the user over a predetermined time period (e.g., usage over last 14 days) may be converted to a numeric value and normalized to a value between 0 and 1. Likewise, height of a user may be converted to a numeric value and normalized to a value between 0 and 1. Further, gender and whether or not the user used the sauna on a previous day may be converted to normalized numeric values (e.g., 0 or 1).

The following example illustrates modeling training data for a plurality of users. Normalized value is as follows:

Normalized value = (value − smallest value in set)/(largest value in set − smallest value in set)

For the height criteria, the data is as follows:

Sally: 5'6" (5.500 ft)
John: 5' 8" (5.667 ft)
Jane: 5' 10" (5.833 ft)

John's normalized height = (5.667 − 5.5)/(5.833 − 5.5) = 0.167/0.333 = 0.50

-continued (Sally's = 0, Jane's = 1)

The following Python Code may be used to generate the coefficients:

```
#Read in the data
data=pandas.read_csv ('data_set.csv', index_col=False)
#Separate out just the input columns
columns=['male', 'height', 'time_minus_wakeup']
X_train=data [columns]
#Identify the column you want to predict (temperature at time=0)
y_train=data ['t0']
regression=sm.OLS (y_train, X_train).fit( )
print (regression.summary( ))
```

The following is an example output of OLS Regression Results:

TABLE 3

| | | | |
|---|---|---|---|
| Dep. Variable: | t0 | R-squared: | 0.436 |
| Model: | OLS | Adj. R-squared: | 0.410 |
| Method: | Least Squares | F-statistic: | 16.83 |
| Date: | Tue, 12 Dec. 2023 | Prob (F-statistic): | 1.95e–26 |
| Time: | 14:54:13 | Log-Likelihood: | –233.15 |
| No. Observations: | 274 | AIC: | 492.3 |
| Df Residuals: | 261 | BIC: | 539.3 |
| Df Model: | 12 | | |

Further results of one example are as follows:

| | coeff | Std err | t | P > \|t\| | [0.025 | 0.975] |
|---|---|---|---|---|---|---|
| Const | 98.6585 | 0.218 | 453.296 | 0.000 | 98.230 | 99.087 |
| Male | 1.5279 | 0.232 | 6.572 | 0.000 | 1.070 | 1.986 |
| Height | –2.5668 | 0.293 | –8.760 | 0.000 | –3.144 | –1.990 |
| Time_minus_wakeup | 0.9545 | 0.189 | 5.043 | 0.000 | 0.582 | 1.327 |

The following is further information about one example regression:

| | | | |
|---|---|---|---|
| Omnibus: | 27.704 | Durbin-Watson: | 1.113 |
| Prob(Omnibus): | 0.000 | Jarque-Bera (JB): | 43.270 |
| Skew: | –0.626 | Prob(JB): | 4.02e–10 |
| Kurtosis: | 4.491 | Cond. No. | 39.4 |

Figure 8:
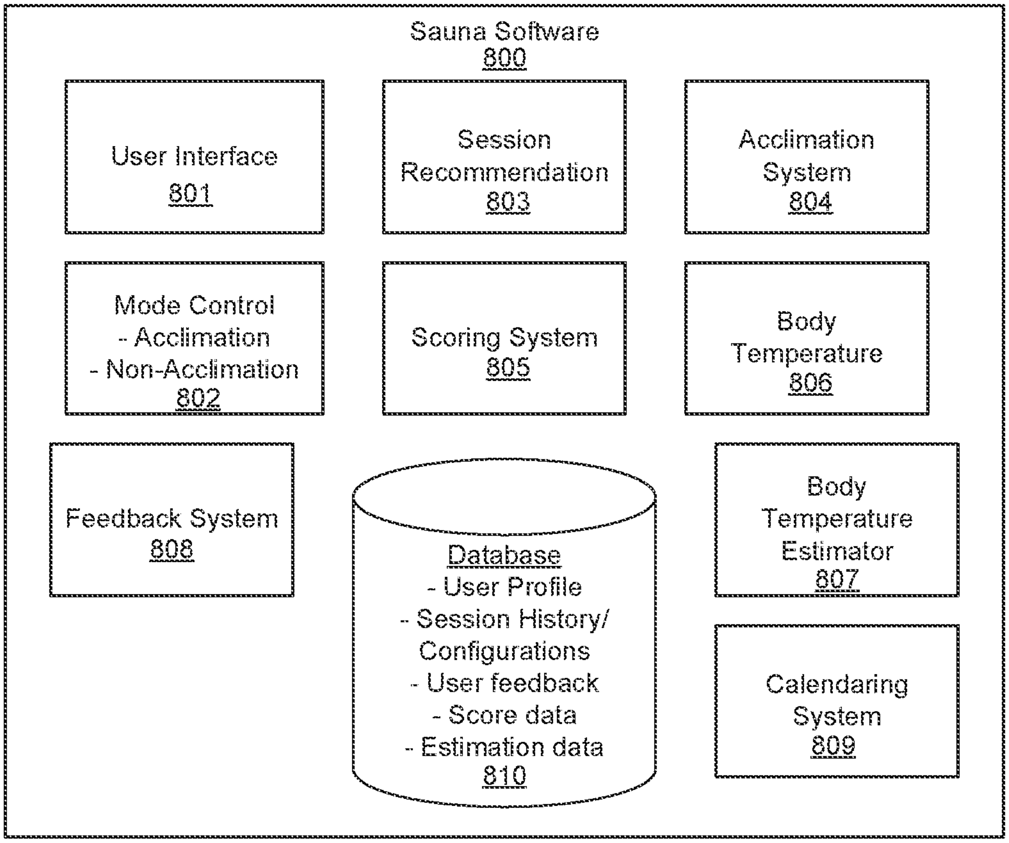
FIG. 8 illustrates an example software system according to an embodiment.

FIG. 8 illustrates an example software system according to an embodiment. It is to be understood that sauna software comprising some or all of the various software features shown in FIG. 8 may be implemented on a computing device local or remote to the sauna, such as in an "App" installed on a mobile phone, tablet computer, or smart watch or on a dedicated sauna computer system, for example. Some or all of the features described herein may be implemented in a cloud computer system, for example. In some embodiments, users have access to some or all of the features described herein based on access rights, where users may pay for some or all of the features described herein on a feature by feature basis, for example.

In this example, sauna software 800 includes user interface (UI) software 801. UI 801 may perform processing related to user interaction, such as receiving data inputs from a user or sending display outputs or messages to the user, for example. A mode control software component 802 may detect when a user is a new user and configure the software into either acclimation mode or non-acclimation mode as described above. Session recommendation software component 803 may include code for performing recommendations and suggestions of sessions as described above. Acclimation system software 804 may include code for managing and performing the acclimation techniques described above. Scoring system software 805 may determine scores for users as described above. Scoring system 805 may invoke body temperature software 806 to receive body temperature data (e.g., measured or estimated), for example. In some embodiments, software 800 may include body temperature estimator software 807 (e.g., a machine learning model, linear regression model, or the like) to determine body temperature of a user during use of the sauna, for example. In some embodiments, sauna software 800 includes feedback system software to adjust sauna configurations based on user feedback as described above. Additionally, sauna software 800 may include a calendaring system software 809 to perform the calendaring functionality and techniques described above. Finally, in this example, sauna software 800 may include one or more databases 810 comprising user profile information, session history and configurations, user feedback, score data (e.g., accumulated points for users), and estimation data (e.g., training data and coefficients/weights).

Example Hardware

Figure 9:
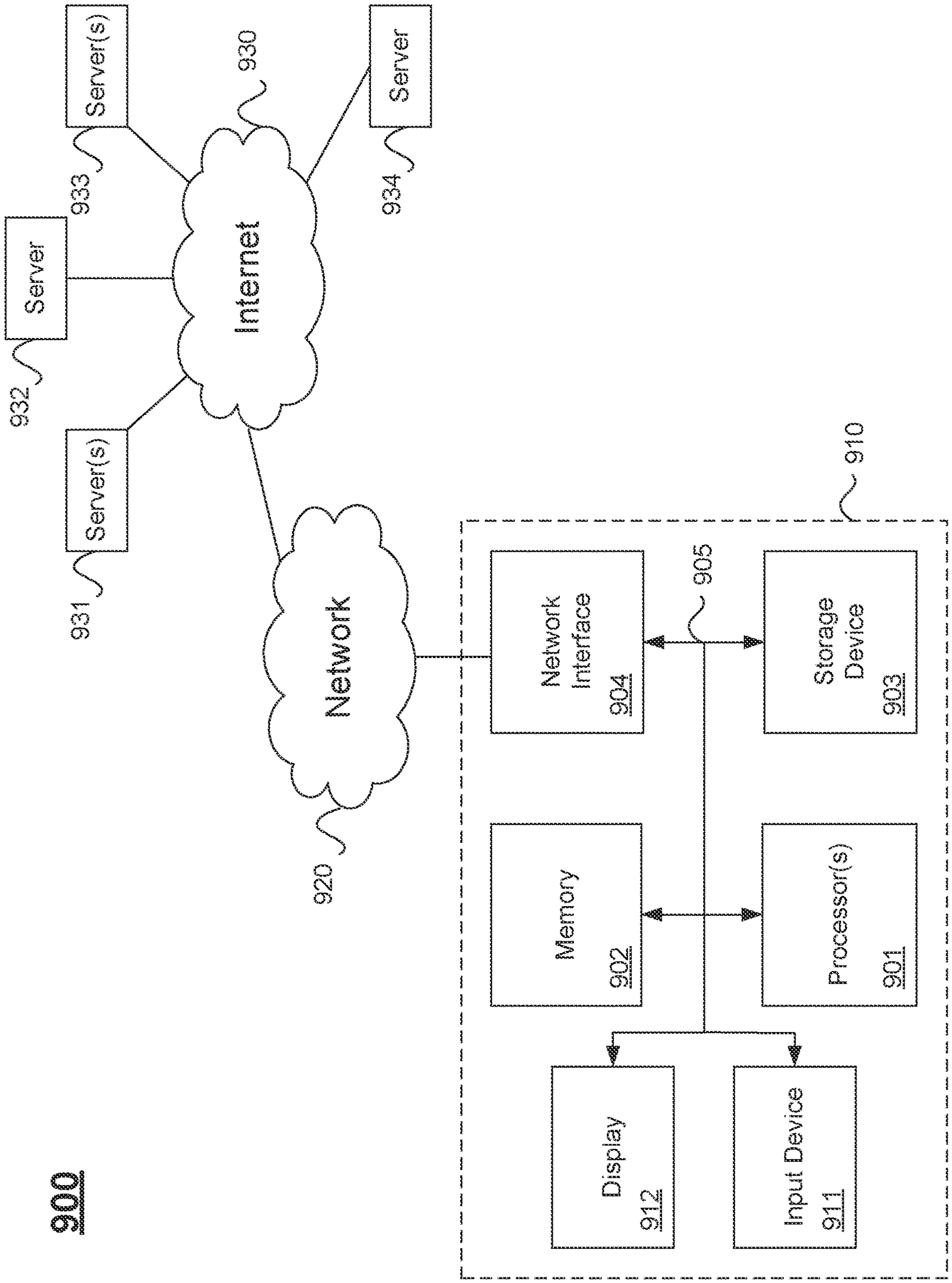
FIG. 9 illustrates example computer hardware for implementing various embodiments.

FIG. 9 illustrates example computer hardware for implementing various embodiments. The following hardware description is merely one example. It is to be understood that a variety of computers topologies may be used to implement the above-described techniques. An example computer system 910 is illustrated in FIG. 9. Computer system 910 includes a bus 905 or other communication mechanism for communicating information, and one or more processor(s) 901 coupled with bus 905 for processing information. Computer system 910 also includes memory 902 coupled to bus 905 for storing information and instructions to be executed by processor 901, including information and instructions for performing some of the techniques described above, for example. Memory 902 may also be used for storing programs executed by processor(s) 901. Possible implementations of memory 902 may be, but are not limited to, random access memory (RAM), read only memory (ROM), or both. A storage device 903 is also provided for storing information and instructions. Common forms of storage devices include, for example, a hard drive, a magnetic disk, an optical disk, a CD-ROM, a DVD, solid state disk, a flash or other non-volatile memory, a USB memory card, or any other electronic storage medium from which a computer can read. Storage device 903 may include source code, binary code, or software files for performing the techniques above, for example. Storage device 903 and memory 902 are both examples of non-transitory computer readable storage mediums (aka, storage media).

In some systems, computer system 910 may be coupled via bus 905 to a display 912 for displaying information to a computer user. An input device 911 such as a keyboard, touchscreen, and/or mouse is coupled to bus 905 for communicating information and command selections from the user to processor 901. The combination of these components allows the user to communicate with the system. In some systems, bus 905 represents multiple specialized buses for coupling various components of the computer together, for example.

Computer system 910 also includes a network interface 904 coupled with bus 905. Network interface 904 may provide two-way data communication between computer system 910 and a local network 920. Network 920 may represent one or multiple networking technologies, such as Ethernet, local wireless networks (e.g., WiFi), or cellular networks, for example. The network interface 904 may be a wireless or wired connection, for example. Computer system 910 can send and receive information through the network interface 904 across a wired or wireless local area network, an Intranet, or a cellular network to the Internet 930, for example. In some embodiments, a frontend (e.g., a browser), for example, may access data and features on backend software systems that may reside on multiple different hardware servers on-premise 931 or across the network 930 (e.g., an Extranet or the Internet) on servers 932-934. One or more of servers 932-934 may also reside in a cloud computing environment, for example.

Further Example Embodiments

Each of the following non-limiting features in the following examples may stand on its own or may be combined in various permutations or combinations with one or more of the other features in the examples below. In various embodiments, the present disclosure may be implemented as a system, method, or computer readable medium.

Embodiments of the present disclosure may include systems, methods, or computer readable media. In one embodiment, the present disclosure includes computer system comprising: at least one processor and at least one non-transitory computer readable medium (e.g., memory) storing computer executable instructions that, when executed by the at least one processor, cause the computer system to perform a method as described herein and in the following examples. In another embodiment, the present disclosure includes a non-transitory computer-readable medium storing computer-executable instructions that, when executed by at least one processor, perform a method as described herein and in the following examples.

In one embodiment, the present disclosure includes a method of controlling a sauna comprising: receiving, in a controller circuit configured to control said sauna, a first initiation signal; in response to the first initiation signal, configuring the sauna in a warm up mode; increasing a temperature inside the sauna; detecting a first predefined temperature inside the sauna; in response to detecting the first predefined temperature, maintaining the first predefined temperature; receiving, in the controller circuit, a second initiation signal; and in response to receiving the second initiation signal, increasing the temperature inside the sauna and maintaining the temperature inside the sauna at or below a second predefined temperature.

In one embodiment, the method further comprises, after the second initiation signal, disabling a plurality of electronic circuits in the sauna to reduce electromagnetic radiation inside the sauna.

In one embodiment, during a first time period after the first initiation signal and before detecting the first predefined temperature inside the sauna, generating a first signal indicating a first warm up mode of operation; upon detecting the first predefined temperature inside the sauna, generating a second signal indicating completion of the warm up mode; and during a second time period after the second initiation signal, generating a third signal indicating a low-EMF mode of operation.

In one embodiment, the plurality of disabled electronic circuits comprise a wireless communication circuit coupled to the controller.

In one embodiment, the first initiation signal is received in the controller through the wireless communication circuit.

In one embodiment, the first initiation signal is embedded in a Bluetooth signal and the wireless communication circuit is a Bluetooth communication circuit.

In one embodiment, the first initiation signal is embedded in an 802.11 signal and the wireless communication circuit is a 802.11 communication circuit.

In one embodiment, after the second initiation signal and before disabling a plurality of electronic circuits, sending, by the controller circuit, session information comprising: an indication the sauna is in session, a plurality of sauna settings, and a finish time for a session.

In one embodiment, the method further comprising after a predefined sauna session is complete, enabling the plurality of electronic circuits in the sauna.

In one embodiment, the second initiation signal is received from a user in the controller circuit.

In one embodiment, the second initiation signal is received through an input device coupled to the controller circuit.

In one embodiment, the second initiation signal is embedded in a wireless signal received in the wireless communication circuit.

In one embodiment, during a first time period after the first initiation signal and before detecting the first predefined temperature inside the sauna, generating a first signal indicating a first warm up mode of operation; upon detecting the first predefined temperature inside the sauna, generating a second signal indicating completion of the warm up mode.

In one embodiment, the first and second signals are displayed on a touch screen display coupled to the sauna.

In one embodiment, one or more of the first and second signals are colored lights.

In one embodiment, one or more of the first and second signals are sounds.

In one embodiment, the method further comprising: storing, for a particular sauna, temperature data over a plurality of cycles of a time period occurring after the first initiation signal and before detecting the first predefined temperature inside the sauna; and determining, based on the stored temperature data, a warm up time for a particular sauna.

In one embodiment, the first predefined temperature is between 90 degrees Fahrenheit and 120 degrees Fahrenheit and wherein the second predefined temperature is above 120 degrees Fahrenheit.

In one embodiment, the present disclosure includes a sauna comprising: a controller circuit configured to control said sauna; a plurality of heaters; one or more temperature sensors; and a plurality of electronic circuits, wherein: a first initiation signal is received in the controller circuit; in response to the first initiation signal, the controller circuit configures the sauna in a warm up mode; the controller circuit configures the plurality of heaters to increase a temperature inside the sauna; and the temperature detectors, after a first time period, detect a first predefined temperature inside the sauna; in response to detecting the first predefined temperature, the controller circuit configures the plurality of heaters to maintain the first temperature; after a second time period, the controller circuit receives a second initiation signal; in response to receiving the second initiation signal, increasing the temperature inside the sauna above the first predefined temperature and not to exceed a second temperature greater than the first predefined temperature.

In one embodiment, the present disclosure includes a sauna cloud server system comprising: one or more computer systems wherein the one or more computer systems are coupled over a network to a plurality of saunas at a plurality of different locations, the one or more computer systems comprising: one or more processors; a non-transitory computer-readable medium storing computer-executable instructions that, when executed by at least one processor, perform a method, the method comprising: storing profile information for a plurality of users of the plurality of saunas; storing location information for the plurality of saunas, the location information specifying locations of the plurality of saunas; storing configuration information for the plurality of saunas, the configuration information specifying hardware and software elements for each of the plurality of saunas; associating profile information, location information, and configuration information for particular saunas of the plurality of saunas; receiving control information from a first remote computer system external to the one or more computer systems; and controlling one or more of the plurality of saunas using the control information.

In one embodiment, the one or more computer systems are cloud based computer systems comprising one or more web servers.

In one embodiment, the first remote computer system is a mobile device executing a mobile application for generating the control information.

In one embodiment, the plurality of saunas comprise a plurality of heaters, the method further comprising: storing temperature data for the plurality of saunas; and controlling the heaters for particular saunas based on a portion of the stored temperature data associated with the particular sauna.

In one embodiment, the portion of the stored temperature data corresponds to a sauna warm up time.

In one embodiment, the portion of the stored temperature data corresponds to a sauna session.

In one embodiment, the profile information comprises previous sessions of the plurality of users and corresponding saunas.

In one embodiment, the profile information comprises one or more of: height, weight, gender, age, prior sauna use history for the user over a predetermined time period, whether or not the user used the sauna on a previous day, and a time difference between when the user woke up on a particular day and a start time of the particular use of the sauna on the particular day.

In one embodiment, the system further comprising storing a plurality of algorithms for controlling the plurality of saunas.

In one embodiment, different algorithms are compatible with different saunas based on the configuration information.

In one embodiment, particular configuration information for a particular sauna is applied to one or more algorithms to modify the one or more algorithms for the particular sauna.

In one embodiment, the location information comprises information about a home or business where a particular sauna is located.

In one embodiment, the configuration information comprises, for each sauna, information about one or more of: components, software versions, hardware configurations, and software configurations.

In one embodiment, the system further comprising storing environmental information associated with each sauna.

In one embodiment, the system further comprising executing a calendaring software program, wherein a plurality of users schedule time, using a mobile device, to use the plurality of saunas.

In one embodiment, the calendaring software program is used with the location information to schedule maintenance of the plurality of saunas so that the plurality of users scheduled times do not overlap with scheduled maintenance of the plurality of saunas.

In one embodiment, a first instance of a calendaring software program is associated with a first entity profile and a second instance of a calendaring software program is associated with a second entity profile, wherein the first entity and the second entity are different businesses.

In one embodiment, the system further comprising automatically executing a warm up mode on one or more of the plurality of saunas based on the calendaring software program.

In one embodiment, the system further comprising: determining, based on the configuration information, that one or more saunas have fans; and automatically activating the fans between sauna sessions on the one or more saunas based on the calendaring software program.

In one embodiment, the system further comprising alerting a cleaning crew between sauna sessions on one or more of the plurality of saunas based on the calendaring software program.

In one embodiment, the system further comprising executing a recommendation software program to suggest sessions and operating conditions for particular users based on each user's profile information.

In one embodiment, the system further comprising executing self-test based on the configuration information.

In one embodiment, the present disclosure includes a method of controlling a plurality of saunas comprising: on one or more computer systems, wherein the one or more computer systems are coupled over a network to the plurality of saunas at a plurality of different locations, storing profile information for a plurality of users of the plurality of saunas; storing location information for the plurality of saunas, the location information specifying locations of the plurality of saunas; storing configuration information for the plurality of saunas, the configuration information specifying hardware and software elements for each of the plurality of saunas; associating profile information, location information, and configuration information for particular saunas of the plurality of saunas; receiving control information from a first remote computer system; and controlling one or more of the plurality of saunas using the control information.

In one embodiment, the present disclosure includes a method for use in a sauna comprising: storing profile information about a user of the sauna; monitoring use of the sauna by the user associated with the profile over a plurality of days; and generating a score based on usage of the sauna over the plurality of days, wherein the score increases for a particular day of use of the sauna and the score decreases for a particular day of non-use of the sauna, wherein the score increases based on an increase in a body temperature of the user during a particular use of the sauna.

In one embodiment, the score increases on the particular day of use when the increase in body temperature is above a threshold during the particular use of the sauna.

In one embodiment, the score comprises a ratio of accumulated points associated with a user over the plurality of days and a total points possible for a time period.

In one embodiment, the total points possible for a time period is one of a plurality of multiples of a maximum points from a single use of the sauna.

In one embodiment, the plurality of multiples is user selectable.

In one embodiment, the body temperature is core body temperature.

In one embodiment, the increase in the body temperature of the user during the particular use of the sauna is used to estimate an increase in heat shock protein production in the user.

In one embodiment, the increase in the body temperature of the user during the particular use of the sauna is used to estimate heat acclimation of the user.

In one embodiment, an amount the score increases during the particular use of the sauna comprises a sum comprising a plurality of body temperature values corresponding to increases in body temperature at a plurality of time intervals.

In one embodiment, the plurality of body temperature values are increases in body temperature after entering the sauna.

In one embodiment, the time intervals are minutes.

In one embodiment, an amount the score increases during the particular use of the sauna is based in part on a sum, over a plurality of time intervals, of a product subtracted from a first constant, wherein the product is a plurality of body temperature values corresponding to increases in body temperature at each of the plurality of time intervals multiplied by a second constant.

In one embodiment, a minimum increase in body temperature is set such that the product is greater than or equal to the second constant.

In one embodiment, an amount the score increases during the particular use of the sauna has a maximum value.

In one embodiment, when a preexisting score is a maximum score and a current score is less than the maximum, increasing an amount the score increases based on the increase in the body temperature of the user during the particular use of the sauna.

In one embodiment, when a preexisting score is a maximum score and a current score is less than the maximum, decreasing an amount the score decreases based on non-use.

In one embodiment, the score comprises a previous score minus a loss value corresponding to a time between sauna sessions plus a gained value from the particular use of the sauna.

In one embodiment, the increase in body temperature is measured.

In one embodiment, the increase in body temperature is estimated.

In one embodiment, the increase in body temperature is estimated based, at least in part, on a time difference between when the user woke up on a particular day and a start time of the particular use of the sauna on the particular day.

In one embodiment, the increase in body temperature is estimated based, at least in part, on prior sauna use history for the user over a predetermined time period.

In one embodiment, the increase in body temperature is estimated based, at least in part, on a height of the user.

In one embodiment, the increase in body temperature is estimated based, at least in part, on a gender of the user.

In one embodiment, the increase in body temperature is estimated based, at least in part, on whether or not the user used the sauna on a previous day.

In one embodiment, the increase in body temperature is estimated based, at least in part, on two or more of: a time difference between when the user woke up on a particular day and a start time of the particular use of the sauna on the particular day, a prior sauna use history for the user over a predetermined time period, and a height of the user.

In one embodiment, the method further comprising training a predictive engine to perform the estimation.

In one embodiment, the predictive engine comprises a neural network.

In one embodiment, the predictive engine comprises a linear regression.

In one embodiment, the estimation comprises a linear regression having a plurality of coefficients, wherein the coefficients correspond to at least one or more of: a normalized time difference between when the user woke up on a particular day and a start time of the particular use of the sauna on the particular day, a normalized prior sauna use history for the user over a predetermined time period, a normalized height of the user, a normalized gender of the user, and a normalized value corresponding to whether or not the user used the sauna on a previous day.

In one embodiment, the method further comprising, at an end of the particular use of the sauna: prompting the user to input feedback; receiving an input from the user; and configuring a subsequent session duration and subsequent session maximum temperature based on the input.

In one embodiment, the present disclosure includes a method for use in a sauna comprising: prompting a user to input one or more of: a fitness level and a sweat frequency; receiving a response to the prompt; determining a duration and a maximum temperature based, at least in part, on the response to the prompt; configuring the sauna to operate at or below the determined maximum temperature for the determined duration.

In one embodiment, said prompting comprises a fitness level and a sweat frequency, and wherein the response comprises an indication of the fitness level and an indication of the sweat frequency.

In one embodiment, the method further comprising determining that the user is a new user of the sauna, the method further comprising: entering an acclimation mode; and generating a sequence of sauna sessions over a plurality of days, the sequence of sauna sessions each having an associated duration and an associated maximum temperature.

In one embodiment, the sequence of sauna sessions successively increase one or more of: the associated duration and the associated temperature.

In one embodiment, the sequence of sauna sessions alternately increase the associated duration and the associated temperature.

In one embodiment, the method further comprising generating a score based on usage of the sauna over the plurality of days, wherein the score increases for each day of use of the sauna and the score decreases for each day of non-use of the sauna.

In one embodiment, the method further comprising: during a current sauna session, determining an increase in the score from the current sauna session and a decrease in the score from one or more days of non-use of the sauna, wherein, when the increase is less than the decrease during a current sauna session: determining a remaining time so that the increase equals the decrease; and generating a message to the user indicating the remaining time.

In one embodiment, the method further comprising, at an end of a completed sauna session: prompting the user to input feedback; receiving an input from the user; and configuring a subsequent session duration and subsequent session maximum temperature based on the input.

In one embodiment, the input corresponds to one of: an indication the completed sauna session was too hot, an indication the completed sauna session was too long, and one or more indications the completed sauna session was neither too hot nor too long.

In one embodiment, prompting further includes prompting the user to enter an age and receiving an age of the user, wherein determining the duration and the temperature is further based on the age, and wherein when the age is greater than a threshold, the determined duration is a particular duration that is less than a determined duration for an age below the threshold and/or the determined temperature is a particular temperature that is less than a determined temperature for an age below the threshold.

In one embodiment, the method further comprising: generating a plurality of fitness predictions over a plurality of days, wherein the fitness predictions indicate one or more gains in fitness, one or more constant fitness, and one or more losses in fitness over the plurality of days; and displaying the plurality of fitness predictions in a display in sequence from highest gain in fitness to highest loss in fitness.

In one embodiment, the plurality of fitness predictions are displayed in a calendar.

In one embodiment, different fitness predictions of the plurality of fitness predictions are displayed using different colors.

In one embodiment, the present disclosure includes a system, device, or method comprising a predictive engine to estimate a body temperature using a linear regression. In one embodiment, the estimation comprises a linear regression having a plurality of coefficients, wherein the coefficients correspond to at least one or more of: a normalized time difference between when the user woke up on a particular day and a start time of the particular use of the sauna on the particular day, a normalized prior sauna use history for the user over a predetermined time period, a normalized height of the user, a normalized gender of the user, and a normalized value corresponding to whether or not the user used the sauna on a previous day.

In one embodiment, the present disclosure includes a system, apparatus, device, method, or computer readable medium comprising instructions to perform a method to perform any combination of: (a) controlling a sauna comprising: receiving, in a controller circuit configured to control said sauna, a first initiation signal; in response to the first initiation signal, configuring the sauna in a warm up mode; increasing a temperature inside the sauna; detecting a first predefined temperature inside the sauna; in response to detecting the first predefined temperature, maintaining the first predefined temperature; receiving, in the controller circuit, a second initiation signal; and in response to receiving the second initiation signal, increasing the temperature inside the sauna and maintaining the temperature inside the sauna at or below a second predefined temperature, (b) for one or more computer systems coupled over a network to a plurality of saunas at a plurality of different locations, storing profile information for a plurality of users of the plurality of saunas; storing location information for the plurality of saunas, the location information specifying locations of the plurality of saunas; storing configuration information for the plurality of saunas, the configuration information specifying hardware and software elements for each of the plurality of saunas; associating profile information, location information, and configuration information for particular saunas of the plurality of saunas; receiving control information from a first remote computer system external to the one or more computer systems; and controlling one or more of the plurality of saunas using the control information, (c) storing profile information about a user of the sauna; monitoring use of the sauna by the user associated with the profile over a plurality of days; and generating a score based on usage of the sauna over the plurality of days, wherein the score increases for a particular day of use of the sauna and the score decreases for a particular day of non-use of the sauna, wherein the score increases based on an increase in a body temperature of the user during a particular use of the sauna, and/or (d) prompting a user to input one or more of: a fitness level and a sweat frequency; receiving a response to the prompt; determining a duration and a maximum temperature based, at least in part, on the response to the prompt; configuring the sauna to operate at or below the determined maximum temperature for the determined duration.

The above description illustrates various embodiments along with examples of how aspects of some embodiments may be implemented. The above examples and embodiments should not be deemed to be the only embodiments, and are presented to illustrate the flexibility and advantages of some embodiments as defined by the following claims. Based on the above disclosure and the following claims, other arrangements, embodiments, implementations and equivalents may be employed without departing from the scope hereof as defined by the claims.

What is claimed is:

1. A method of controlling a sauna comprising:

receiving, in a controller circuit configured to control said sauna, a first initiation signal;

in response to the first initiation signal, configuring the sauna in a warm up mode;

increasing a temperature inside the sauna;

detecting a first predefined temperature inside the sauna;

in response to detecting the first predefined temperature, maintaining the first predefined temperature;

receiving, in the controller circuit, a second initiation signal; and in response to receiving the second initiation signal, increasing the temperature inside the sauna and maintaining the temperature inside the sauna at or below a second predefined temperature, after the second initiation signal, disabling a plurality of electronic circuits in the sauna to reduce electromagnetic radiation inside the sauna.

2. The method of claim 1, wherein:

during a first time period after the first initiation signal and before detecting the first predefined temperature inside the sauna, generating a first signal indicating a first warm up mode of operation;

upon detecting the first predefined temperature inside the sauna, generating a second signal indicating completion of the warm up mode; and during a second time period after the second initiation signal, generating a third signal indicating a low-EMF mode of operation.

3. The method of claim 1, wherein the plurality of disabled electronic circuits comprise a wireless communication circuit coupled to the controller.

4. The method of claim 3, wherein the first initiation signal is received in the controller through the wireless communication circuit.

5. The method of claim 4, wherein the first initiation signal is embedded in a Bluetooth signal and the wireless communication circuit is a Bluetooth communication circuit.

6. The method of claim 4, wherein the first initiation signal is embedded in an 802.11 signal and the wireless communication circuit is a 802.11 communication circuit.

7. The method of claim 1, wherein, after the second initiation signal and before disabling a plurality of electronic circuits, sending, by the controller circuit, session information comprising: an indication the sauna is in session, a plurality of sauna settings, and a finish time for a session.

8. The method of claim 1, further comprising after a predefined sauna session is complete, enabling the plurality of electronic circuits in the sauna.

9. The method of claim 1, wherein the second initiation signal is received from a user in the controller circuit.

10. The method of claim 9, wherein the second initiation signal is received through an input device coupled to the controller circuit.

11. The method of claim 9, wherein the second initiation signal is embedded in a wireless signal received in the wireless communication circuit.

12. The method of claim 1, further comprising:
- storing, for a particular sauna, temperature data over a plurality of cycles of a time period occurring after the first initiation signal and before detecting the first predefined temperature inside the sauna;
- determining, based on the stored temperature data, a warm up time for a particular sauna.

13. The method of claim 1, wherein the first predefined temperature is between 90 degrees Fahrenheit and 120 degrees Fahrenheit and wherein the second predefined temperature is above 120 degrees Fahrenheit.

14. A method of controlling a sauna comprising:
- receiving, in a controller circuit configured to control said sauna, a first initiation signal;
- in response to the first initiation signal, configuring the sauna in a warm up mode;
- increasing a temperature inside the sauna;
- detecting a first predefined temperature inside the sauna;
- in response to detecting the first predefined temperature, maintaining the first predefined temperature;
- receiving, in the controller circuit, a second initiation signal; and
- in response to receiving the second initiation signal, increasing the temperature inside the sauna and maintaining the temperature inside the sauna at or below a second predefined temperature, wherein:
- during a first time period after the first initiation signal and before detecting the first predefined temperature inside the sauna, generating a first signal indicating a first warm up mode of operation;
- upon detecting the first predefined temperature inside the sauna, generating a second signal indicating completion of the warm up mode.

15. The method of claim 14, wherein the first and second signals are displayed on a touch screen display coupled to the sauna.

16. The method of claim 14, wherein one or more of the first and second signals are colored lights.

17. The method of claim 14, wherein one or more of the first and second signals are sounds.

18. A sauna comprising:
- a controller circuit configured to control said sauna;
- a plurality of heaters;
- one or more temperature sensors; and
- a plurality of electronic circuits, wherein:
- a first initiation signal is received in the controller circuit;
- in response to the first initiation signal,
  - the controller circuit configures the sauna in a warm up mode;
  - the controller circuit configures the plurality of heaters to increase a temperature inside the sauna; and
  - the temperature detectors, after a first time period, detect a first predefined temperature inside the sauna;
- in response to detecting the first predefined temperature, the controller circuit configures the plurality of heaters to maintain the first temperature;
- after a second time period, the controller circuit receives a second initiation signal;
- in response to receiving the second initiation signal, increasing the temperature inside the sauna above the first predefined temperature and not to exceed a second temperature greater than the first predefined temperature,
- after the second initiation signal, disabling a plurality of electronic circuits in the sauna to reduce electromagnetic radiation inside the sauna.

19. The sauna of claim 18, wherein:
- during a first time period after the first initiation signal and before detecting the first predefined temperature inside the sauna, generating a first signal indicating a first warm up mode of operation;
- upon detecting the first predefined temperature inside the sauna, generating a second signal indicating completion of the warm up mode; and
- during a second time period after the second initiation signal, generating a third signal indicating a low-EMF mode of operation.

* * * * *